United States Patent
Kino et al.

(10) Patent No.: US 10,392,673 B2
(45) Date of Patent: Aug. 27, 2019

(54) METHOD OF PRODUCING (-)-ROTUNDONE

(71) Applicant: T. HASEGAWA CO., LTD., Tokyo (JP)

(72) Inventors: Kuniki Kino, Tokyo (JP); Toshiki Furuya, Chiba (JP)

(73) Assignee: T. HASEGAWA CO., LTD., Tokyo (JP)

( * ) Notice: Subject to any disclaimer, the term of this patent is extended or adjusted under 35 U.S.C. 154(b) by 100 days.

(21) Appl. No.: 15/609,260

(22) Filed: May 31, 2017

(65) Prior Publication Data

US 2017/0356059 A1    Dec. 14, 2017

(30) Foreign Application Priority Data

Jun. 10, 2016 (JP) .................. 2016-116213

(51) Int. Cl.
| | |
|---|---|
| *C12N 9/02* | (2006.01) |
| *C07C 13/52* | (2006.01) |
| *C07C 49/215* | (2006.01) |
| *C12N 15/66* | (2006.01) |
| *C12P 7/26* | (2006.01) |

(52) U.S. Cl.
CPC ............ *C12Y 117/99* (2013.01); *C07C 13/52* (2013.01); *C07C 49/215* (2013.01); *C12N 15/66* (2013.01); *C12P 7/26* (2013.01); *C12Y 111/02004* (2013.01); *C12Y 114/14* (2013.01); *C07C 2602/30* (2017.05)

(58) Field of Classification Search
CPC ....................................... C12N 1/20
USPC ..................................... 435/252.3
See application file for complete search history.

(56) References Cited

U.S. PATENT DOCUMENTS

| | | |
|---|---|---|
| 2003/0068788 A1 | 4/2003 | Buckel et al. |
| 2013/0089904 A1 | 4/2013 | Schilling et al. |

FOREIGN PATENT DOCUMENTS

| | | |
|---|---|---|
| JP | 6-16516 | 1/1994 |
| JP | 2004-529651 | 9/2004 |
| JP | 2010-158177 | 7/2010 |
| JP | 5758000 | 8/2015 |

OTHER PUBLICATIONS

Partial European Search Report dated Oct. 23, 2017 in European Application No. 17174027.7.
Takase et al., "Cytochrome P450 CYP71BE5 in grapevine (*Vitis vinifera*) catalyzes the formation of the spicy aroma compound (-)—rotundone", Journal of Experimental Botany, vol. 67, No. 3, Nov. 20, 2015, pp. 787-798.
Hannemann et al., "Cytochrome P450 systems-biological variations of electron transport chains", Biochimica et Biophysica Acta, vol. 1770, No. 3, 2007, pp. 330-344.
Itoh et al., "Simultaneous expression of ferredoxin, ferredoxin reductase and P450 in COS7 cells", Biochimica et Biophysica Acta, vol. 1318, No. 1-2, 1997, pp. 284-290.
Kapadia et al., "Sesquiterpenoids from the essential oil of cyperus rotundus", Tetrahedron Letters, vol. 8, No. 47, (1967), pp. 4661-4667.
Ishihara et al., "Guaiane sesquiterpenes from agarwood", Phytochemistry, vol. 30, No. 10, (1991), pp. 3343-3347.
Wood et al., "From Wine to Pepper: Rotundone, an Obscure Sesquiterpene, Is a potent Spicy Aromo Compound", Journal of Agricultural and Food Chemistry, vol. 56, No. 10, (2008), pp. 3738-3744.
Huang et al., "Production of the Pepper Aroma Compound, (—)-Rotundone, by Aerial Oxidation of α-Guaiene", Journal of Agricultural and Food Chemistry, No. 62, (2014), pp. 10809-10815.

*Primary Examiner* — Tekchand Saidha
(74) *Attorney, Agent, or Firm* — Wenderoth, Lind & Ponack, L.L.P.

(57) ABSTRACT

The present invention provides a method of producing (−)-rotundone from α-guaiene. The method includes the steps of: (1) allowing a cytochrome P450 protein to act on α-guaiene, which cytochrome P450 belongs to the CYP152 family and is capable of oxidizing the methylene group at position 3 of α-guaiene to the carbonyl group; and/or (2) allowing a cytochrome P450 protein to act on α-guaiene in the presence of an electron transfer protein capable of transferring electrons to the cytochrome P450 protein, which cytochrome P450 belongs to the CYP152, CYP106, or CYP107 family and is capable of oxidizing the methylene group at position 3 of α-guaiene to the carbonyl group.

8 Claims, 1 Drawing Sheet
Specification includes a Sequence Listing.

SEQUENCE LISTING

```
<160> NUMBER OF SEQ ID NOS: 23

<210> SEQ ID NO 1
<211> LENGTH: 417
<212> TYPE: PRT
<213> ORGANISM: Bacillus subtilis

<400> SEQUENCE: 1

Met Asn Glu Gln Ile Pro His Asp Lys Ser Leu Asp Asn Ser Leu Thr
1               5                   10                  15

Leu Leu Lys Glu Gly Tyr Leu Phe Ile Lys Asn Arg Thr Glu Arg Tyr
            20                  25                  30

Asn Ser Asp Leu Phe Gln Ala Arg Leu Leu Gly Lys Asn Phe Ile Cys
```

```
            35                  40                  45
Met Thr Gly Ala Glu Ala Ala Lys Val Phe Tyr Asp Thr Asp Arg Phe
 50                  55                  60

Gln Arg Gln Asn Ala Leu Pro Lys Arg Val Gln Lys Ser Leu Phe Gly
 65                  70                  75                  80

Val Asn Ala Ile Gln Gly Met Asp Gly Ser Ala His Ile His Arg Lys
                     85                  90                  95

Met Leu Phe Leu Ser Leu Met Thr Pro Pro His Gln Lys Arg Leu Ala
                    100                 105                 110

Glu Leu Met Thr Glu Glu Trp Lys Ala Ala Val Thr Arg Trp Glu Lys
                    115                 120                 125

Ala Asp Glu Val Val Leu Phe Glu Glu Ala Lys Glu Ile Leu Cys Arg
                    130                 135                 140

Val Ala Cys Tyr Trp Ala Gly Val Pro Leu Lys Glu Thr Glu Val Lys
145                 150                 155                 160

Glu Arg Ala Asp Asp Phe Ile Asp Met Val Asp Ala Phe Gly Ala Val
                    165                 170                 175

Gly Pro Arg His Trp Lys Gly Arg Arg Ala Arg Pro Arg Ala Glu Glu
                    180                 185                 190

Trp Ile Glu Val Met Ile Glu Asp Ala Arg Ala Gly Leu Leu Lys Thr
                    195                 200                 205

Thr Ser Gly Thr Ala Leu His Glu Met Ala Phe His Thr Gln Glu Asp
210                 215                 220

Gly Ser Gln Leu Asp Ser Arg Met Ala Ala Ile Glu Leu Ile Asn Val
225                 230                 235                 240

Leu Arg Pro Ile Val Ala Ile Ser Tyr Phe Leu Val Phe Ser Ala Leu
                    245                 250                 255

Ala Leu His Glu His Pro Lys Tyr Lys Glu Trp Leu Arg Ser Gly Asn
                    260                 265                 270

Ser Arg Glu Arg Glu Met Phe Val Gln Glu Val Arg Arg Tyr Tyr Pro
                    275                 280                 285

Phe Gly Pro Phe Leu Gly Ala Leu Val Lys Lys Asp Phe Val Trp Asn
                    290                 295                 300

Asn Cys Glu Phe Lys Lys Gly Thr Ser Val Leu Leu Asp Leu Tyr Gly
305                 310                 315                 320

Thr Asn His Asp Pro Arg Leu Trp Asp His Pro Asp Glu Phe Arg Pro
                    325                 330                 335

Glu Arg Phe Ala Glu Arg Glu Glu Asn Leu Phe Asp Met Ile Pro Gln
                    340                 345                 350

Gly Gly Gly His Ala Glu Lys Gly His Arg Cys Pro Gly Glu Gly Ile
                    355                 360                 365

Thr Ile Glu Val Met Lys Ala Ser Leu Asp Phe Leu Val His Gln Ile
                    370                 375                 380

Glu Tyr Asp Val Pro Glu Gln Ser Leu His Tyr Ser Leu Ala Arg Met
385                 390                 395                 400

Pro Ser Leu Pro Glu Ser Gly Phe Val Met Ser Gly Ile Arg Arg Lys
                    405                 410                 415

Ser

<210> SEQ ID NO 2
<211> LENGTH: 407
<212> TYPE: PRT
<213> ORGANISM: Bacillus subtilis
```

-continued

```
<400> SEQUENCE: 2

Met Gln Met Glu Lys Leu Met Phe His Pro His Gly Lys Glu Phe His
1               5                   10                  15

His Asn Pro Phe Ser Val Leu Gly Arg Phe Glu Glu Pro Ile
            20                  25                  30

His Arg Phe Glu Leu Lys Arg Phe Gly Ala Thr Tyr Pro Ala Trp Leu
        35                  40                  45

Ile Thr Arg Tyr Asp Asp Cys Met Ala Phe Leu Lys Asp Asn Arg Ile
    50                  55                  60

Thr Arg Asp Val Lys Asn Val Met Asn Gln Glu Gln Ile Lys Met Leu
65                  70                  75                  80

Asn Val Ser Glu Asp Ile Asp Phe Val Ser Asp His Met Leu Ala Lys
                85                  90                  95

Asp Thr Pro Asp His Thr Arg Leu Arg Ser Leu Val His Gln Ala Phe
            100                 105                 110

Thr Pro Arg Thr Ile Glu Asn Leu Arg Gly Ser Ile Glu Gln Ile Ala
        115                 120                 125

Glu Gln Leu Leu Asp Glu Met Glu Lys Glu Asn Lys Ala Asp Ile Met
130                 135                 140

Lys Ser Phe Ala Ser Pro Leu Pro Phe Ile Val Ile Ser Glu Leu Met
145                 150                 155                 160

Gly Ile Pro Lys Glu Asp Arg Ser Gln Phe Gln Ile Trp Thr Asn Ala
                165                 170                 175

Met Val Asp Thr Ser Glu Gly Asn Arg Glu Leu Thr Asn Gln Ala Leu
            180                 185                 190

Arg Glu Phe Lys Asp Tyr Ile Ala Lys Leu Ile His Asp Arg Arg Ile
        195                 200                 205

Lys Pro Lys Asp Asp Leu Ile Ser Lys Leu Val His Ala Glu Glu Asn
210                 215                 220

Gly Ser Lys Leu Ser Glu Lys Glu Leu Tyr Ser Met Leu Phe Leu Leu
225                 230                 235                 240

Val Val Ala Gly Leu Glu Thr Thr Val Asn Leu Leu Gly Ser Gly Thr
                245                 250                 255

Leu Ala Leu Leu Gln His Lys Lys Glu Cys Glu Lys Leu Lys Gln Gln
            260                 265                 270

Pro Glu Met Ile Ala Thr Ala Val Glu Glu Leu Leu Arg Tyr Thr Ser
        275                 280                 285

Pro Val Val Met Met Ala Asn Arg Trp Ala Ile Glu Asp Phe Thr Tyr
290                 295                 300

Lys Gly His Ser Ile Lys Arg Gly Asp Met Ile Phe Ile Gly Ile Gly
305                 310                 315                 320

Ser Ala Asn Arg Asp Pro Asn Phe Phe Glu Asn Pro Glu Ile Leu Asn
                325                 330                 335

Ile Asn Arg Ser Pro Asn Arg His Ile Ser Phe Gly Phe Gly Ile His
            340                 345                 350

Phe Cys Leu Gly Ala Pro Leu Ala Arg Leu Glu Gly His Ile Ala Phe
        355                 360                 365

Lys Ala Leu Leu Lys Arg Phe Pro Asp Ile Glu Leu Ala Val Ala Pro
370                 375                 380

Asp Asp Ile Gln Trp Arg Lys Asn Val Phe Leu Arg Gly Leu Glu Ser
385                 390                 395                 400

Leu Pro Val Ser Leu Ser Lys
                405
```

<210> SEQ ID NO 3
<211> LENGTH: 404
<212> TYPE: PRT
<213> ORGANISM: Bacillus cereus

<400> SEQUENCE: 3

```
Met Ala Ser Pro Glu Asn Val Ile Leu Val His Glu Ile Ser Lys Leu
1               5                   10                  15

Lys Thr Lys Glu Glu Leu Trp Asn Pro Tyr Glu Trp Tyr Gln Phe Met
            20                  25                  30

Arg Asp Asn His Pro Val His Tyr Asp Glu Glu Gln Asp Val Trp Asn
        35                  40                  45

Val Phe Leu Tyr Glu Asp Val Asn Arg Val Leu Ser Asp Tyr Arg Leu
    50                  55                  60

Phe Ser Ser Arg Arg Glu Arg Arg Gln Phe Ser Ile Pro Pro Leu Glu
65                  70                  75                  80

Thr Arg Ile Asn Ile Asn Ser Thr Asp Pro Pro Glu His Arg Asn Val
                85                  90                  95

Arg Ser Ile Val Ser Lys Ala Phe Thr Pro Arg Ser Leu Glu Gln Trp
            100                 105                 110

Lys Pro Arg Ile Gln Ala Ile Ala Asn Glu Leu Val Gln His Ile Gly
        115                 120                 125

Lys Tyr Ser Glu Val Asn Ile Val Glu Glu Phe Ala Ala Pro Leu Pro
    130                 135                 140

Val Thr Val Ile Ser Asp Leu Leu Gly Val Pro Thr Thr Asp Arg Lys
145                 150                 155                 160

Lys Ile Lys Ala Trp Ser Asp Ile Leu Phe Met Pro Tyr Ser Lys Glu
                165                 170                 175

Lys Phe Asn Asp Leu Asp Val Glu Lys Gly Ile Ala Leu Asn Glu Phe
            180                 185                 190

Lys Ala Tyr Leu Leu Pro Ile Val Gln Glu Lys Arg Tyr His Leu Thr
        195                 200                 205

Asp Asp Ile Ile Ser Asp Leu Ile Arg Ala Glu Tyr Glu Gly Glu Arg
    210                 215                 220

Leu Thr Asp Glu Glu Ile Val Thr Phe Ser Leu Gly Leu Leu Ala Ala
225                 230                 235                 240

Gly Asn Glu Thr Thr Thr Asn Leu Ile Ile Asn Ser Phe Tyr Cys Phe
                245                 250                 255

Leu Val Asp Ser Pro Gly Thr Tyr Lys Glu Leu Arg Glu Glu Pro Thr
            260                 265                 270

Leu Ile Ser Lys Ala Ile Glu Glu Val Leu Arg Tyr Arg Phe Pro Ile
        275                 280                 285

Thr Leu Ala Arg Arg Ile Thr Glu Asp Thr Asn Ile Phe Gly Pro Leu
    290                 295                 300

Met Lys Lys Asp Gln Met Val Val Ala Trp Val Ser Ala Ala Asn Leu
305                 310                 315                 320

Asp Glu Lys Lys Phe Ser Gln Ala Ser Lys Phe Asn Ile His Arg Ile
                325                 330                 335

Gly Asn Glu Lys His Leu Thr Phe Gly Lys Gly Pro His Phe Cys Leu
            340                 345                 350

Gly Ala Pro Leu Ala Arg Leu Glu Ala Glu Ile Ala Leu Thr Thr Phe
        355                 360                 365

Ile Asn Ala Phe Glu Lys Ile Ala Leu Ser Pro Ser Phe Asn Leu Glu
```

```
    370                 375                 380

Gln Cys Ile Leu Glu Asn Glu Gln Thr Leu Lys Phe Leu Pro Ile Cys
385                 390                 395                 400

Leu Lys Thr Gln

<210> SEQ ID NO 4
<211> LENGTH: 410
<212> TYPE: PRT
<213> ORGANISM: Bacillus cereus

<400> SEQUENCE: 4

Met Lys Lys Leu Thr Phe Asn Asp Leu Asn Ser Pro Glu Thr Met Arg
1               5                   10                  15

Asn Pro Ile Met Phe Tyr Lys Asn Leu Met Glu Gln Lys Glu Arg Phe
            20                  25                  30

Phe His Ile Asp Asp Phe Tyr Gly Met Gly Gly Ala Trp Val Val Phe
        35                  40                  45

His Tyr Asp Asp Val Val Ala Ile Leu Lys Asp Ser Arg Phe Ile Lys
    50                  55                  60

Asp Leu Arg Lys Phe Thr Pro Pro His Tyr Lys Gln Asn Pro Ile Glu
65                  70                  75                  80

Glu Asn Thr Ala Val Ser Lys Leu Phe Glu Trp Leu Met Asn Met Pro
                85                  90                  95

Asn Met Leu Thr Val Asp Pro Pro Asp His Thr Arg Leu Arg Arg Leu
            100                 105                 110

Val Ser Lys Ser Phe Thr Pro Arg Met Ile Glu Asp Leu Arg Pro Arg
        115                 120                 125

Ile Gln Gln Ile Ala Asp Glu Leu Leu Asp Val Val Gln Glu Gln Arg
    130                 135                 140

Lys Met Glu Ile Ile Ala Asp Phe Ala Tyr Pro Leu Pro Ile Ile Val
145                 150                 155                 160

Ile Ser Glu Met Leu Gly Ile Pro Ala Thr Asp Arg Asn Gln Phe Arg
                165                 170                 175

Ala Trp Thr Gln Glu Leu Met Lys Ala Ser Val Asp Pro Gly Gln Gly
            180                 185                 190

Thr Thr Val Thr Ala Thr Leu Glu Lys Phe Ile Asn Tyr Ile Glu Ile
        195                 200                 205

Leu Phe Asn Glu Lys His Leu Asn Pro Ser Asp Asp Leu Ile Ser Ala
    210                 215                 220

Leu Val Gln Ala Lys Glu Gln Glu Asp Lys Leu Ser Lys Asn Glu Leu
225                 230                 235                 240

Leu Ser Thr Ile Trp Leu Leu Ile Ile Ala Gly His Glu Thr Thr Val
                245                 250                 255

Asn Leu Ile Ser Asn Gly Val Leu Ala Leu Leu Gln His Pro Glu Gln
            260                 265                 270

Met Asn Leu Leu Arg Gln Asp Pro Ser Leu Leu Ala Ser Ala Val Asp
        275                 280                 285

Glu Leu Leu Arg Tyr Ala Gly Pro Ile Met Phe Ser Ser Arg Phe Ala
    290                 295                 300

Ser Glu Asp Val Thr Ile His Gly Asn Arg Ile Arg Lys Gly Glu Leu
305                 310                 315                 320

Val Leu Leu Ser Leu Thr Ala Ala Asn Ile Asp Pro Asn Ile Phe Pro
                325                 330                 335

Tyr Pro Glu Glu Leu Asn Ile Ser Arg Glu Glu Asn Asn His Leu Ala
```

```
            340             345             350
Phe Gly Ala Gly Ile His Gln Cys Leu Gly Ala Pro Leu Ala Arg Leu
        355                 360                 365

Glu Gly Gln Ile Ala Leu Asp Thr Leu Leu Lys Arg Leu Pro Asn Leu
    370                 375                 380

Arg Leu Ala Ile Glu Ala Asp Gln Leu Ile Tyr Asn His Ser Lys Ile
385                 390                 395                 400

Arg Ser Leu Ala Ser Leu Pro Val Ile Phe
            405                 410

<210> SEQ ID NO 5
<211> LENGTH: 1254
<212> TYPE: DNA
<213> ORGANISM: Bacillus subtilis

<400> SEQUENCE: 5
atgaatgagc agattccaca tgacaaaagt ctcgataaca gtctgacact gctgaaggaa      60
gggtatttat ttattaaaaa cagaacagag cgctacaatt cagatctgtt tcaggcccgt     120
ttgttgggaa aaactttat ttgcatgact ggcgctgagg cggcgaaggt gttttatgat      180
acggatcgat tccagcggca aacgctttg cctaagcggg tgcagaaatc gctgtttggt      240
gttaatgcga ttcagggaat ggatggcagc gcgcatatcc atcggaagat gcttttctg      300 tcattgatga caccgccgca tcaaaaacgt ttggctgagt tgatgacaga ggagtggaaa     360
gcagcagtca agatgggaa gaaggcagat gaggttgtgt tatttgaaga agcaaaagaa      420
atcctgtgcc gggtagcgtg ctattgggca ggtgttccgt gaaggaaac ggaagtcaaa      480 gagagagcgg atgacttcat tgacatggtc gacgcgttcg gtgctgtggg accgcggcat     540
tggaaaggaa gaagagcaag gccgcgtgcg gaagagtgga ttgaagtcat gattgaagat     600
gctcgtgccg gcttgctgaa aacgacttcc ggaacagcgc tgcatgaaat ggcttttcac     660
acacaagaag atgaagcca gctggattcc cgcatggcag ccattgagct gattaatgta      720
ctgcggccta ttgtcgccat ttcttacttt ctggtgtttt cagctttggc gcttcatgag     780
catccgaagt ataaggaatg gctgcggtct ggaaacagcc gggaaagaga atgtttgtg      840 caggaggtcc gcagatatta tccgttcggc ccgtttttag gggcgcttgt caaaaaagat     900
tttgtatgga ataactgtga gtttaagaag gcacatcgg tgctgcttga tttatatgga     960
acgaaccacg accctcgtct atgggatcat cccgatgaat ccggccgga cgatttgcg     1020 gagcgggaag aaaatctgtt tgatatgatt cctcaaggcg gggggcacgc cgagaaaggc    1080
caccgctgtc caggggaagg cattacaatt gaagtcatga agcgagcct ggatttcctc     1140 gtccatcaga ttgaatacga tgttccggaa caatcactgc attacagtct cgccagaatg    1200
ccatcattgc ctgaaagcgg cttcgtaatg agcggaatca gacgaaaaag ttaa           1254

<210> SEQ ID NO 6
<211> LENGTH: 1224
<212> TYPE: DNA
<213> ORGANISM: Bacillus subtilis

<400> SEQUENCE: 6
atgcaaatgg aaaaattgat gtttcatccg catggtaaag agtttcatca caatcctttt      60
tcagttttag gacgatttag agaggaagag cccattcacc gatttgaatt aaaacggttc     120
ggagccacat atccggcctg gttaattacc cgatacgatg attgtatggc cttttttaaaa    180 gacaatcgaa ttacaagaga cgtaaaaaat gtgatgaacc aagaacaaat caaaatgctc     240
```

-continued

```
aacgttagtg aagatatcga ttttgtatcc gatcatatgc tggcaaaaga cacacctgac    300
catacccgcc tgagatcact tgttcatcaa gcatttactc cccgaaccat tgaaaatctg    360
cgcggcagca ttgaacaaat tgctgaacag cttttagatg aaatggaaaa agaaaataaa    420
gcggatatca tgaaatcctt cgcttcccct ttgcctttta ttgttatatc tgaattgatg    480
ggaatcccaa aagaagatcg gtcacagttt caaatctgga ccaatgcgat ggttgatacc    540
tctgaaggta atagagagct gacaaatcag gcccttcgtg aatttaaaga ttatatcgct    600
aagctgatcc atgacagaag aataaagcca aaagacgatt taatcagcaa acttgtgcat    660
gctgaggaaa acggcagcaa gttaagcgaa aaagagctct attcgatgct gttcttgctc    720
gttgtagccg gccttgaaac aactgttaac ttactcggct caggcaccct cgcattgctg    780
cagcacaaga aggaatgtga gaagctcaag cagcagcctg aaatgatcgc tacagcggtt    840
gaagaattgc tgcgatacac ctcacctgtc gttatgatgg caaatcggtg ggccatcgaa    900
gactttacat ataaggggca ttcgatcaaa agaggagaca tgatttttat aggcatcgga    960
tctgccaatc gcgacccgaa ttttttgag aaccccgaaa tattaaatat aaatcggtcg    1020
cctaatagac atatttcttt tggttttggc attcatttct gcttaggagc gcctcttgcc   1080
aggctggaag gccacattgc atttaaagca cttttgaaga gatttcctga tattgaactt   1140
gcggttgcac ctgatgacat tcaatggaga aaaaatgtct tttaagaggg attagaaagt   1200
ctccctgttt cactttcaaa ataa                                           1224

<210> SEQ ID NO 7
<211> LENGTH: 1215
<212> TYPE: DNA
<213> ORGANISM: Bacillus cereus

<400> SEQUENCE: 7
atggcttcgc ctgaaaatgt gattttagtt catgaaattt caaagctgaa aacgaaagag      60
gaattgtgga atccgtatga gtggtatcaa tttatgaggg ataatcaccc cgtacattat    120
gatgaagagc aagatgtttg gaatgtattt ttgtatgagg acgtaaatcg tgttttatca    180
gactatcgcc tgttttcaag tagaagggag cgaagacaat tctcaatccc tcctttagag    240
actcgaatca atattaattc tactgatcca ccagaacatc gcaatgtacg ttctatcgtt    300
tctaaagcat ttactccaag gagtttagaa caatggaaac ctcgaataca ggctatcgca    360
aatgaacttg tacaacatat tggaaaatat agtgaagtta atatcgttga agagtttgct    420
gctcctttac ctgttactgt tatatccgat ttgttaggag tgccaacaac tgaccgcaaa    480
aaaattaaag catggtctga tattttattt atgccgtata gtaaagaaaa gtttaatgat    540
ctggatgtag aaaaggggat agcactaaat gaatttaaag catatcttct accaatcgtt    600
caggaaaaga gataccattt aaccgatgat attatctcag atttaatacg agctgaatat    660
gaaggcgaaa gattaactga tgaagaaatt gttacttttt cattgggttt attagcggct    720
ggtaatgaaa caactacaaa tttaattatt aatagttttt actgtttctt agtggattca    780
ccaggaacat ataaagaatt aagagaagaa cctacattaa tttcaaaagc aattgaggaa    840
gtattacgct atcgttttcc cattacatta gctaggagaa ttacagagga tacaaatata    900
tttggccctt taatgaaaaa ggatcaaatg gtggttgcgt gggtaagtgc agcaaattta    960
gatgagaaaa agttttcaca agcctctaaa tttaatatac accgaatagg aaatgaaaag    1020
catttaacat ttggtaaagg tcctcacttt tgcttagggg caccacttgc acgtttagaa    1080
```

```
gctgagattg cattaactac ctttataaat gcttttgaaa agatagcatt atctccatcg    1140
ttcaatttag aacaatgtat attggaaaat gaacaaactt tgaaattctt acctatctgc    1200
ttaaaaactc aataa                                                    1215

<210> SEQ ID NO 8
<211> LENGTH: 1233
<212> TYPE: DNA
<213> ORGANISM: Bacillus cereus

<400> SEQUENCE: 8
atgaaaaaac taacttttaa cgatttgaac tcgccggaaa ctatgcgtaa tcccattatg      60
ttctataaaa accttatgga gcaaaaagag cgtttctttc acattgatga cttttatgga    120
atgggagggg catgggttgt atttcactat gatgatgtgg ttgctatttt aaaagattcc    180
cgttttatca aagatttacg aaaattcaca ccgcctcatt ataagcagaa tcccattgag    240
gagaatacag cagtgagtaa actatttgaa tggcttatga atatgccgaa tatgcttacg    300
gtagatcctc ctgatcatac tcgcctacgt cggctagtct ctaaatcctt cacaccacgt    360
atgattgaag accttcgtcc tcgtattcag caaattgccg acgaattgtt ggatgttgta    420
caggaacaaa gaaagatgga aattattgca gactttgctt acccactacc cattattgtc    480
atttcagaga tgcttgggat tcccgccact gatcgaaatc agtttcgcgc atggacacaa    540
gaactgatga aggcctcagt ggatcctggt caagggacta cagtgacagc aacacttgaa    600
aagtttatta attatattga atattgtttt aacgaaaaac acctaaatcc tagtgatgat    660
ttgataagcg cgctagttca agcaaaagag caagaagaca agttgagtaa gaacgagctt    720
ctttcgacaa tttggcttct tattatcgct ggacatgaaa cgacagttaa tctaattagt    780
aatggtgtac tagcgttact tcaacatcct gaacaaatga atttactaag gcaagatcct    840
tctctgctgg cttccgctgt cgacgaactt ttacgctatg ctggtccaat tatgtttagt    900
agccgttttg ctagtgaaga tgtgacaata catggaaata gaatacgtaa aggtgaattg    960
gttctactct ccctgactgc tgcaaatatt gatccgaaca tatttcctta tccagaggaa    1020
ttgaatattt cacgggagga gaataaccat ttagcctttg gggctggtat acatcaatgt    1080
ttgggagctc cattggcgcg tttagaagga caaattgcat tagacacttt gttaaagagg    1140
ctacctaatc tccgcctagc aatcgaagca gatcaattga tttataacca tagtaaaatt    1200
cgttcccttg caagtctacc agttattttc taa                                1233

<210> SEQ ID NO 9
<211> LENGTH: 3825
<212> TYPE: DNA
<213> ORGANISM: Pseudomonas putida

<400> SEQUENCE: 9
tccggcgact accaaagcgg tataaacaca tgggagtgcg tgctaagtga acgcaaacga      60
caacgtggtc atcgtcggta ccggactggc tggcgttgag gtcgccttcg gcctgcgcgc    120
cagcggctgg gaaggcaata tccggttggt gggggatgcg acggtaattc cccatcacct    180
accaccgcta tccaaagctt acttggccgg caaagccaca gcggaaagcc tgtacctgag    240
aaccccagat gcctatgcag cgcagaacat ccaactactc ggaggcacac aggtaacggc    300
tatcaaccgc gaccgacagc aagtaatcct atcggatggc cggcactggg attacgaccg    360
gctggtattg gctaccggag ggcgtccaag acccctaccg gtggccagtg cgcagttggc    420
aaaggcgaac aactttcgat acctgcgcac actcgaggac gccgagtgca ttcgccggca    480
```

-continued

```
gctgattgcg gataaccgtc tggtggtgat tggtggcggc tacattggcc ttgaagtggc    540
tgccaccgcc atcaaggcga acatgcacgt caccctgctt gatacggcag cccgggttct    600
ggagcgggtt accgccccgc cggtatcggc cttttacgag cacctacacc gcgaagccgg    660
cgttgacata cgaaccggca cgcaggtgtg cgggttcgat atgtcgaccg accaacagaa    720
ggttactgcc gtcctctgcg aggacggcac aaggctgcca gcggatctgg taatcgccgg    780
gattggcctg ataccaaact gcgagttggc cagtgcggcc ggcctgcagg ttgataacgg    840
catcgtgatc aacgaacaca tgcagacctc tgatcccttg atcatggccg tcggcgactg    900
tgcccgattt cacagtcagc tctatgaccg ctgggtgcgt atcgaatcgg tgcccaatgc    960
cttggagcag gcacgaaaga tcgccgccat cctctgtggc aaggtgccac gcgatgaggc   1020
ggcgccctgg ttctggtccg atcagtatga gatcggattg aagatggtcg gactgtccga   1080
agggtacgac cggatcattg tccgcggctc tttggcgcaa cccgacttca gcgttttcta   1140
cctgcaggga gaccgggtat tggcggtcga tacagtgaac cgtccagtgg agttcaacca   1200
gtcaaaacaa ataatcacgg atcgtttgcc ggttgaacca aacctactcg gtgacgaaag   1260
cgtgccgtta aggaaatca tcgccgccgc caaagctgaa ctgagtagtg cctgaaatct   1320
atacccacaa taaatcaccg ttttgcccca tagcgtgtga ggataaacag atgtctaaag   1380
tagtgtatgt gtcacatgat ggaacgcgtc gcgaactgga tgtggcggat ggcgtcagcc   1440
tgatgcaggc tgcagtctcc aatggtatct acgatattgt cggtgattgt ggcggcagcg   1500
ccagctgtgc cacctgccat gtctatgtga acgaagcgtt cacggacaag gtgcccgccg   1560
ccaacgagcg ggaaatcggc atgctggagt gcgtcacggc cgaactgaag ccgaacagca   1620
ggctctgctg ccagatcatc atgacgcccg agctggatgg catcgtggtc gatgttcccg   1680
ataggcaatg gtaaaccaca atggtaaacc actgcgagcc aaaacagccg agcaggagcg   1740
cagtccggca acaccttatt aagcacatgc cgaaccctat ttgcagcgct tcatgcctgc   1800
aaagtcccga ttgatgaaat ccgggctcca agcaaggagc ccggaatctc tcaccgccac   1860
gaaatcaatg ccaatcccg ggacttggtt gagacgtccg tttctccact acgactttgt   1920
cgcaatgatc tcctcatgct cagatccgaa ggatctctat agatcataca gccaggctgt   1980
atctggagaa gtccaaggtt catctggtct gtgatgccaa tgactcgccc tcaagcctcg   2040
ttttgtcagt gagagtagtc acctgatgca acagcgtctc actcaacgcc tgcgccgcgc   2100
tggatagctg atgcccagcc tggtgcagca ggccgacgcg acgcgacacc tgtggctcgc   2160
tcagcggtag gcagcgggcg cccagttctt ccatctgctg ccggcacagt gcggcacgg   2220
cgctgacgcc gagtgaacgc aaacgacaac gtggtcatcg tcggtaccgg actggctggc   2280
gttgaggtcg ccttcggcct gcgcgccagc ggctgggaag gcaatatccg gttggtgggg   2340
gatgcgacgg taattcccca tcacctacca ccgctatcca aagcttactt ggccggcaaa   2400
gccacagcgg aaagcctgta cctgagaacc ccagatgcct atgcagcgca gaacatccaa   2460
ctactcggag gcacacaggt aacggctatc aaccgcgacc gacagcaagt aatcctatcg   2520
gatggccggg cactggatta cgaccggctg gtattggcta ccggagggcg tccaagaccc   2580
ctaccggtgg ccagtggcgc agttggaaag gcgaacaact ttcgatacct gcgcacactc   2640
gaggacgccg agtgcattcg ccggcagctg attgcggata accgtctggt ggtgattggt   2700
ggcggctaca ttggccttga agtggctgcc accgccatca aggcgaacat gcacgtcacc   2760
ctgcttgata cggcagcccg ggttctggag cgggttaccg ccccgccggt atcggccttt   2820
```

```
tacgagcacc tacaccgcga agccggcgtt gacatacgaa ccggcacgca ggtgtgcggg   2880
ttcgagatgt cgaccgacca acagaaggtt actgccgtcc tctgcgagga cggcacaagg   2940
ctgccagcgg atctggtaat cgccgggatt ggcctgatac caaactgcga gttggccagt   3000
gcggccggcc tgcaggttga taacggcatc gtgatcaacg aacacatgca gacctctgat   3060
cccttgatca tggccgtcgg cgactgtgcc cgatttcaca gtcagctcta tgaccgctgg   3120
gtgcgtatcg aatcggtgcc caatgccttg gagcaggcac gaaagatcgc cgccatcctc   3180
tgtggcaagg tgccacgcga tgaggcggcg ccctggttct ggtccgatca gtatgagatc   3240
ggattgaaga tggtcggact gtccgaaggg tacgaccgga tcattgtccg cggctctttg   3300
gcgcaacccg acttcagcgt tttctacctg cagggagacc gggtattggc ggtcgataca   3360
gtgaaccgtc cagtggagtt caaccagtca aacaaataa tcacggatcg tttgccggtt   3420
gaaccaaacc tactcggtga cgaaagcgtg ccgttaaagg aaatcatcgc cgccgccaaa   3480
gctgaactga gtagtgcctg aatgtctaaa gtagtgtatg tgtcacatga tggaacgcgt   3540
cgcgaactgg atgtggcgga tggcgtcagc ctgatgcagg ctgcagtctc caatggtatc   3600
tacgatattg tcggtgattg tggcggcagc gccagctgtg ccacctgcca tgtctatgtg   3660
aacgaagcgt tcacggacaa ggtgcccgcc gccaacgagc gggaaatcgg catgctggag   3720
tgcgtcacgg ccgaactgaa gccgaacagc aggctctgct gccagatcat catgacgccc   3780
gagctggatg gcatcgtggt cgatgttccc gataggcaat ggtaa              3825
```

<210> SEQ ID NO 10
<211> LENGTH: 107
<212> TYPE: PRT
<213> ORGANISM: Pseudomonas putida

<400> SEQUENCE: 10

```
Met Ser Lys Val Val Tyr Val Ser His Asp Gly Thr Arg Arg Glu Leu
1               5                   10                  15

Asp Val Ala Asp Gly Val Ser Leu Met Gln Ala Val Ser Asn Gly
            20                  25                  30

Ile Tyr Asp Ile Val Gly Asp Cys Gly Gly Ser Ala Ser Cys Ala Thr
        35                  40                  45

Cys His Val Tyr Val Asn Glu Ala Phe Thr Asp Lys Val Pro Ala Ala
    50                  55                  60

Asn Glu Arg Glu Ile Gly Met Leu Glu Cys Val Thr Ala Glu Leu Lys
65                  70                  75                  80

Pro Asn Ser Arg Leu Cys Cys Gln Ile Ile Met Thr Pro Glu Leu Asp
                85                  90                  95

Gly Ile Val Val Asp Val Pro Asp Arg Gln Trp
            100                 105
```

<210> SEQ ID NO 11
<211> LENGTH: 422
<212> TYPE: PRT
<213> ORGANISM: Pseudomonas putida

<400> SEQUENCE: 11

```
Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
            20                  25                  30

Arg Leu Val Gly Asp Ala Thr Val Ile Pro His His Leu Pro Pro Leu
        35                  40                  45
```

Ser Lys Ala Tyr Leu Ala Gly Lys Ala Thr Ala Glu Ser Leu Tyr Leu
 50                  55                  60

Arg Thr Pro Asp Ala Tyr Ala Ala Gln Asn Ile Gln Leu Leu Gly Gly
 65                  70                  75                  80

Thr Gln Val Thr Ala Ile Asn Arg Asp Arg Gln Gln Val Ile Leu Ser
                 85                  90                  95

Asp Gly Arg Ala Leu Asp Tyr Asp Arg Leu Val Leu Ala Thr Gly Gly
             100                 105                 110

Arg Pro Arg Pro Leu Pro Val Ala Ser Gly Ala Val Gly Lys Ala Asn
         115                 120                 125

Asn Phe Arg Tyr Leu Arg Thr Leu Glu Asp Ala Glu Cys Ile Arg Arg
     130                 135                 140

Gln Leu Ile Ala Asp Asn Arg Leu Val Val Ile Gly Gly Gly Tyr Ile
145                 150                 155                 160

Gly Leu Glu Val Ala Ala Thr Ala Ile Lys Ala Asn Met His Val Thr
                165                 170                 175

Leu Leu Asp Thr Ala Ala Arg Val Leu Glu Arg Val Thr Ala Pro Pro
            180                 185                 190

Val Ser Ala Phe Tyr Glu His Leu His Arg Glu Ala Gly Val Asp Ile
        195                 200                 205

Arg Thr Gly Thr Gln Val Cys Gly Phe Glu Met Ser Thr Asp Gln Gln
    210                 215                 220

Lys Val Thr Ala Val Leu Cys Glu Asp Gly Thr Arg Leu Pro Ala Asp
225                 230                 235                 240

Leu Val Ile Ala Gly Ile Gly Leu Ile Pro Asn Cys Glu Leu Ala Ser
                245                 250                 255

Ala Ala Gly Leu Gln Val Asp Asn Gly Ile Val Ile Asn Glu His Met
            260                 265                 270

Gln Thr Ser Asp Pro Leu Ile Met Ala Val Gly Asp Cys Ala Arg Phe
        275                 280                 285

His Ser Gln Leu Tyr Asp Arg Trp Val Arg Ile Glu Ser Val Pro Asn
    290                 295                 300

Ala Leu Glu Gln Ala Arg Lys Ile Ala Ala Ile Leu Cys Gly Lys Val
305                 310                 315                 320

Pro Arg Asp Glu Ala Ala Pro Trp Phe Trp Ser Asp Gln Tyr Glu Ile
                325                 330                 335

Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
        355                 360                 365

Asp Arg Val Leu Ala Val Asp Thr Val Asn Arg Pro Val Glu Phe Asn
    370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
                405                 410                 415

Ala Glu Leu Ser Ser Ala
            420

<210> SEQ ID NO 12
<211> LENGTH: 30
<212> TYPE: DNA
<213> ORGANISM: Artificial Sequence
<220> FEATURE:

<223> OTHER INFORMATION: PCR forward primer for CYP152A1

<400> SEQUENCE: 12
gaattccata tgaatgagca gattccacat                                30

<210> SEQ ID NO 13
<211> LENGTH: 30
<212> TYPE: DNA
<213> ORGANISM: Artificial Sequence
<220> FEATURE:
<223> OTHER INFORMATION: PCR reverse primer for CYP152A1

<400> SEQUENCE: 13
cgcggatcct taacttttc gtctgattcc                                30

<210> SEQ ID NO 14
<211> LENGTH: 24
<212> TYPE: DNA
<213> ORGANISM: Artificial Sequence
<220> FEATURE:
<223> OTHER INFORMATION: PCR forward primer for CYP107K1

<400> SEQUENCE: 14
tgcaaatgga aaaattgatg tttc                                     24

<210> SEQ ID NO 15
<211> LENGTH: 30
<212> TYPE: DNA
<213> ORGANISM: Artificial Sequence
<220> FEATURE:
<223> OTHER INFORMATION: PCR reverse primer for CYP107K1

<400> SEQUENCE: 15
cgcggatcct tattttgaaa gtgaaacagg                               30

<210> SEQ ID NO 16
<211> LENGTH: 30
<212> TYPE: DNA
<213> ORGANISM: Artificial Sequence
<220> FEATURE:
<223> OTHER INFORMATION: PCR forward primer for camA

<400> SEQUENCE: 16
ttccatatgt ctaaagtagt gtatgtgtca                               30

<210> SEQ ID NO 17
<211> LENGTH: 30
<212> TYPE: DNA
<213> ORGANISM: Artificial Sequence
<220> FEATURE:
<223> OTHER INFORMATION: PCR reverse primer for camA

<400> SEQUENCE: 17
cacaagcttt taccattgcc tatcgggaac                               30

<210> SEQ ID NO 18
<211> LENGTH: 30
<212> TYPE: DNA
<213> ORGANISM: Artificial Sequence
<220> FEATURE:
<223> OTHER INFORMATION: PCR forward primer for camB

<400> SEQUENCE: 18
ttccatatga acgcaaacga caacgtggtc                               30

```
<210> SEQ ID NO 19
<211> LENGTH: 30
<212> TYPE: DNA
<213> ORGANISM: Artificial Sequence
<220> FEATURE:
<223> OTHER INFORMATION: PCR reverse primer for camB

<400> SEQUENCE: 19
cacgagctct caggcactac tcagttcagc                                30

<210> SEQ ID NO 20
<211> LENGTH: 30
<212> TYPE: DNA
<213> ORGANISM: Artificial Sequence
<220> FEATURE:
<223> OTHER INFORMATION: PCR forward primer for CYP106(BCE_2659)

<400> SEQUENCE: 20
gaattccata tggcttcgcc tgaaaatgtg                                30

<210> SEQ ID NO 21
<211> LENGTH: 30
<212> TYPE: DNA
<213> ORGANISM: Artificial Sequence
<220> FEATURE:
<223> OTHER INFORMATION: PCR reverse primer for CYP106(BCE_2659)

<400> SEQUENCE: 21
cgcggatcct tattgagttt ttaagcagat                                30

<210> SEQ ID NO 22
<211> LENGTH: 30
<212> TYPE: DNA
<213> ORGANISM: Artificial Sequence
<220> FEATURE:
<223> OTHER INFORMATION: PCR forward primer for CYP107(BCE_2696)(cypA)

<400> SEQUENCE: 22
gaattccata tgaaaaaact aacttttaac                                30

<210> SEQ ID NO 23
<211> LENGTH: 30
<212> TYPE: DNA
<213> ORGANISM: Artificial Sequence
<220> FEATURE:
<223> OTHER INFORMATION: PCR reverse primer for CYP107(BCE_2696)(cypA)

<400> SEQUENCE: 23
ccggaattct tagaaaataa ctggtagact                                30
```

METHOD OF PRODUCING (−)-ROTUNDONE

BACKGROUND

Technical Field

The present invention relates to a method of producing (−)-rotundone useful for flavor and fragrance applications. More specifically, the present invention relates to a method of allowing cytochrome P450 to act on α-guaiene to convert α-guaiene selectively to (−)-rotundone.

Related Art

Natural-type (−)-rotundone ((−)-(3S,5R,8S)-3,8-dimethyl-5-(prop-1-en-2-yl)-3,4,5,6,7,8-hexahydroazulen-1 (2H)-one, hereinafter also simply referred to as "rotundone") is a compound originally isolated from the tuber of *cyperus rotundus*, which is a species of Cyperaceae, and is called "*cyperus* rhizome" as a crude drug, and structurally identified (Tetrahedron Letters, 1967, Vol. 8, No. 47, pp. 4661-4667). Rotundone is also known as a component in Agarwood, which is used for herb medicines in China and for incense burning in Japan (Phytochemistry, 1991, Vol. 30, No. 10, pp. 3343-3347). Rotundone is also reported for use as an insect pest control agent (JP 06-16516 A) because of its repellent effect on insects. Recently, rotundone has been reported to be a component responsible for the spicy, pepper-like aroma of Shiraz wine, which is characterized by a spicy, pepper-like aroma, and grapes for such wine (Journal of Agricultural and Food Chemistry, 2008, Vo. 56, No. 10, pp. 3738-3744). This literature also reports that rotundone is contained at a concentration as low as several ppm in black pepper and white pepper and is an important aroma component of them and rotundone is also contained in a very small amount in spices, such as marjoram, oregano, rosemary, basil, and thyme.

It is also disclosed that rotundone can be used, in combination with rotundol mentioned below, as an aroma compound for flavor or fragrance applications (JP 5758000 B1).

Rotundone can be obtained by extraction from plants. It is difficult, however, to industrialize production of rotundone by extraction techniques because plants contain a limited amount of rotundone and the extraction process is complicated.

JP 5758000 B2 discloses a method of producing rotundol (a compound of which structure is the same as that of rotundone except for having an alcohol group at position 1 in place of the carbonyl group) by allowing a laccase to react with a material containing α-guaiene and/or α-bulnesene in the presence of an oxygen source and also discloses that rotundone is also produced as a by-product in that process (see Examples 3, 4, and 5). However, this method is originally not to produce rotundone and disadvantageous in that it produces various by-products.

Huang et al. (J. Agric. Food Chem. 2014, 62, pp. 10809-10815) reported that rotundone can be produced by air oxidation of α-guaiene. However, its conversion yield is as low as about 15%, and this method is also disadvantageous in that it produces a large amount of epoxy compounds and diketone compounds.

At present, therefore, no method for producing rotundone with high efficiency and high purity has been found yet.

SUMMARY OF INVENTION

An object of the present invention is to provide a method for producing, with high efficiency and high purity, rotundone, a compound which is known for its utility as an aroma compound but has not been known for its high-efficiency production method yet.

Rotundone has a structure the same as α-guaiene except for having a carbonyl group at position 3 in place of a methylene group, and oxidation of the methylene group may yield the carbonyl group. In plants, such as guaiac wood, a Guayacan tree, α-guaiene is contained in a relatively large amount, and thus is available as a starting material. α-Guaiene is also commercially available. Therefore, if rotundone can be produced by selective oxidation of α-guaiene, an efficient process for industrial production of rotundone could be provided.

The present inventors have studied methods for allowing enzymes to selectively oxidize α-guaiene and intensively searched for enzymes capable of achieving such oxidation. As a result, the inventors have found that rotundone can be obtained with high efficiency and high purity by allowing a specific cytochrome P450 protein to act on α-guaiene.

The present invention, therefore, provides a method of producing (−)-rotundone from α-guaiene, the method including the steps of (1) and/or (2): (1) allowing a cytochrome P450 protein to act on α-guaiene, which cytochrome P450 protein belongs to a CYP152 family and is capable of oxidizing the methylene group at position 3 of α-guaiene to the carbonyl group; (2) allowing a cytochrome P450 protein to act on α-guaiene in the presence of an electron transfer protein capable of transferring electrons to the cytochrome P450 protein, which cytochrome P450 protein belongs to a CYP152, CYP106, or CYP107 family and is capable of oxidizing the methylene group at position 3 of α-guaiene to the carbonyl group.

According to the present invention, natural-type rotundone (formula I) useful for flavor and fragrance applications can be produced with high efficiency and high purity by selective oxidation using an enzyme. In the present invention, the use of the enzyme for oxidation makes it possible to produce rotundone from the starting material α-guaiene or from a mixture containing α-guaiene in high yield or at high conversion rate with a reduced amount of by-products. The present invention is also advantageous in that the biological oxidation requiring no metal catalyst will produce no toxic or harmful waste during or after the production and that because of no use of high-concentration oxygen, each production step or operation can be safely performed during the production. In addition, the use of α-guaiene as a starting material, which is a readily available, is suitable for industrial production and economically advantageous. In addition, the natural-type rotundone product obtained according to the present invention can be readily used as a compound for flavor or fragrance composition or a flavoring agent because it contains less impurities and thus has a good aroma.

[Chemical Formula 1]

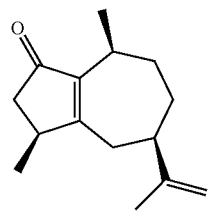

Formula I (−)-rotundone

DETAILED DESCRIPTION

Description of Terminology

Figure 1:
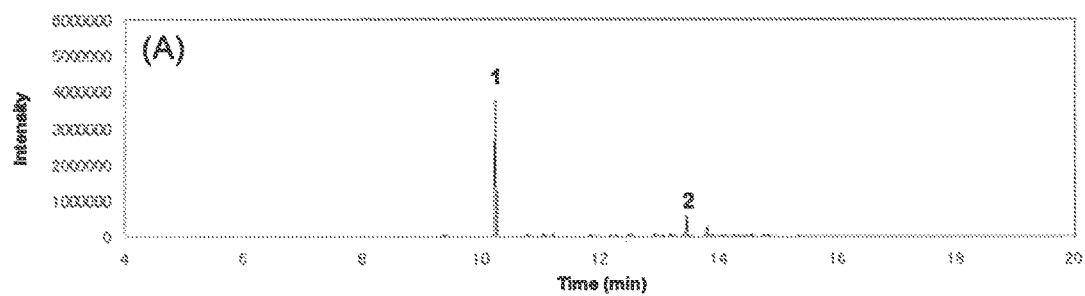
FIG. 1 shows the result of GC-MS analysis of the extraction of the reaction liquid in which α-guaiene was reacted with the *E. coli* cells carrying CYP152A1.

Technical terms used in relation or context with the present invention will be described below. It will be understood that unless otherwise specified, technical terms should be interpreted to have general meanings understandable by those skilled in the art. In some cases, such technical terms are expressed with the term "of the present invention." In such expressions, the term "of the present invention" may have the meaning of "in the present invention" or "for use in the present invention" or the like.

<α-Guaiene>

α-Guaiene [(−)-(1S,4S,7R)-1,4-dimethyl-7-(prop-1-en-2-yl)-1,2,3,4,5,6,7,8-octahydroazulene] (formula II) is a compound used as a starting material in the present invention. This compound may be a commercially available product or a product obtained through extraction from plants, such as guaiac wood, distillation, and arbitrary purification processes.

[Chemical Formula 2]

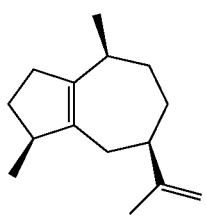

Formula II

<Cytochrome P450 Protein>

Cytochrome P450 proteins are protoheme-containing reduced proteins of a protein family and have monooxygenase activity. Cytochrome P450 proteins are characterized in that when carbon monoxide gas is blown onto them in a reduced state, their absorption spectrum changes to yield a difference spectrum with a maximum at 450 nm (CO difference spectrum). Cytochrome P450 genes are known to exist in most organisms except for some bacteria, such as *Escherichia coli*. Cytochrome P450 proteins are known to be involved in various reactions, such as hydroxylation, epoxidation, and demethylation, and have various roles in vivo, including secondary metabolism, steroidogenesis, foreign substance metabolism, and hydrocarbon utilization.

Cytochrome P450 proteins are classified on the basis of amino acid sequence identity. In principle, those sharing an amino acid sequence identity of 40% or more are classified into the same family, and those sharing an amino acid sequence identity of 55% or more are classified into the same subfamily. Classified ones each have unique classification numbers. The classification numbers include CYP, which represents cytochrome P450, a family number, a subfamily number, and a gene number in this order, in which the gene number is given in order of discovery. Newly discovered cytochrome P450 proteins will be in turn registered in Dr. Nelson's website (http://dmelson.uthsc.edu/CytochromeP450.html). At present, well over 20,000 cytochrome P450 proteins are known.

It has been known from previous studies on substrates for cytochrome P450 proteins and reactions involving these proteins that there are a wide range of reactions and substrates for cytochrome P450 proteins even belonging to the same subfamily. This can be readily conceivable from the fact that, even in the same subfamily, the proteins share an amino acid sequence identity as low as 55%. In addition, some cytochrome P450 proteins exhibit broad substrate specificity whereas others exhibit strict or narrow substrate specificity.

Thus, cytochrome P450 proteins can be said to be a group of a wide variety of proteins, which means that it is difficult to predict, from the classification based on the amino acid sequence, reactions in which individual cytochrome P450 proteins will be involved, substrates for them, and their conversion products.

It is also known that some cytochrome P450 proteins require NAD(P)H-derived electrons for the expression of monooxygenase activity but some do not require them. Examples of cytochrome P450 proteins capable of exhibiting monooxygenase activity in the absence of NAD(P)H-derived electrons include CYP74A (Li et al., Proc. Natl. Acad. Sci. U.S.A. 105 (37), pp. 13883-13888 (2008)) and CYP152 family proteins utilizing hydrogen peroxide, such as CYP152A1 (Matsunaga et al., Lipids, 34, (8), pp. 841-846 (1999)), CYP152B1 (Matsunaga et al., Lipids., 35(4), pp. 365-371 (2000)), and CYP152L1 (Belcher et al., J. Biol Chem., 289(10), pp. 6535-6550).

Other types of cytochrome P450 proteins are known to form a fusion with an electron transfer protein (described below) capable of transferring NAD(P)H-derived electrons to the cytochrome P450 proteins. Examples of such cytochrome P450 proteins include wild-type cytochrome P450 proteins belonging to the CYP102 family (e.g., CYP102A1, CYP102A2, CYP102A3, CYP102D1, which are fused with the reducing domain of FMN and FAD) (such cytochrome P450 proteins are also called self-sufficient cytochrome P450). There are also lots of known artificial fusions of various cytochrome P450 proteins and electron transfer proteins (including fragments of known electron transfer proteins) (e.g., see Helvig, C. and Capdevila, J. H., (2000) Biochemistry, 39, 5196-5205; Sibbesen et al., (1996) J. Biol. Chem. 271, (37), pp. 22462-22469; Nodate et al., (2006) Applied Microbiology and Biotechnology 71(4), pp. 455-462; Li et al., (2007) J. Am. Chem. Soc., 129(43), pp. 12940-12941).

The cytochrome P450 protein of the present invention is characterized by being capable of oxidizing the methylene group at position 3 of α-guaiene. Hereinafter, the oxidation reaction of the methylene group at position 3 of α-guaiene will also be simply referred to as "the oxidation reaction," and the oxidation reaction activity will also be simply referred to as "the oxidation activity."

One or more cytochrome P450 proteins may be used in the oxidation reaction.

The cytochrome P450 protein of the present invention may be one that will or will not use NAD(P)H-derived electrons in the process of oxidizing the methylene group at position 3 of α-guaiene. When the cytochrome P450 protein of the present invention will use NAD(P)H-derived electrons, the cytochrome P450 protein and the electron transfer protein described below may be molecules independent from each other or may form a fusion.

The cytochrome P450 protein of the present invention may belong to any CYP family or subfamily as long as it can oxidize the methylene group at position 3 of α-guaiene. Non-limiting examples of such a family include CYP152, CYP106, and CYP107, and non-limiting examples of such a subfamily include CYP152A and CYP107K.

When a wild-type cytochrome P450 protein is used as the cytochrome P450 protein of the present invention, it may be derived from any organisms having the oxidation activity, such as animals including humans, plants, and bacteria. Examples of bacteria include, but are not limited to, *Bacillus, Pseudomonas*, and *Streptomyces* bacteria, and examples of *Bacillus* bacteria include, but are not limited to, *Bacillus subtilis* and *Bacillus cereus*.

An artificially produced cytochrome P450 protein may also be used as the cytochrome P450 of the present invention. In this case, the cytochrome P450 protein may be biosynthesized or synthesized by chemical peptide synthesis techniques. The biosynthesis may use any materials and methods, such as those shown below as exemplary embodiments. The chemical peptide synthesis may use any known liquid-phase and solid-phase synthesis techniques, which may be performed with reference to "Peptide Gosei No Kiso To Jikken" (Basics and Experiments of Peptide Synthesis), Izumiya et al., Maruzen Publishing Co., Ltd., 1985, and other publications.

The cytochrome P450 protein of the present invention may have any amino acid sequence as long as it is capable of oxidizing the methylene group at position 3 of α-guaiene.

For example, the amino acid sequence of the cytochrome P450 protein of the present invention may be identical to or include the amino acid sequence of a wild-type cytochrome P450 protein. Specific examples of wild-type cytochrome P450 proteins that can be used to achieve the object of the present invention include, but are not limited to, CYP152A1 (SEQ ID NO: 1, GenBank Accession No. CAB 12004.1) and CYP107K1 (SEQ ID NO: 2, GenBank Accession No. ABQ22962.1), which are derived from *Bacillus subtilis*, and CYP106 (BCE_2659) (SEQ ID NO: 3, GenBank Accession No. AAS41573.1) and CYP107 (BCE_2696) (SEQ ID NO: 4, GenBank Accession No. AAS41609.1), which are derived from *Bacillus cereus*.

The cytochrome P450 protein of the present invention may have an amino acid sequence derived by modification (specifically, deletion, substitution, and/or addition) of one or more amino acids in the above wild-type amino acid sequence, as long as the modification does not lose the oxidation activity. The modification may have any effect; the modification may change as desired, i.e., increase or decrease the oxidation activity.

At least one or any number of amino acids may be modified. For example, the number of modified amino acids is 30 or less, 20 or less, 15 or less, 10 or less, or at most several. As used herein, the term "several" means 2, 3, 4, 5, 6, 7, 8, or 9 as the Japanese dictionary Daijirin, Third Edition, edited by Akira Matsumura shows that the corresponding Japanese term means 2, 3 to 5, 6, or so.

Conservative substitution is a preferred example of the amino acid modification. Conservative substitution is the substitution of an amino acid residue or residues with any other residue or residues having similar physicochemical properties and/or structures. It is known in the art what substitution will be conservative for each amino acid. Conservative substitution may be, for example, substitution between amino acids having the same polarity (basicity, acidity, or neutrality), charge, hydrophilicity, and/or hydrophobicity or substitution between aromatic amino acids or aliphatic amino acids. More specifically, examples of conservative substitution include, but are not limited to, substitution of Ala with Ser or Thr, substitution of Arg with Gln, His, or Lys, substitution of Asn with Glu, Gln, Lys, His, or Asp, substitution of Asp with Asn, Glu, or Gln, substitution of Cys with Ser or Ala, substitution of Gln with Asn, Glu, Lys, His, Asp, or Arg, substitution of Glu with Asn, Gln, Lys, or Asp, substitution of Gly with Pro, substitution of His with Asn, Lys, Gln, Arg, or Tyr, substitution of Ile with Leu, Met, Val, or Phe, substitution of Leu with Ile, Met, Val, or Phe, substitution of Lys with Asn, Glu, Gln, His, or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, or Leu.

The amino acid modification may occur in any position as long as it does not lose the oxidation activity. For example, which residue or residues should be modified can be determined on the basis of the three-dimensional structure of the cytochrome P450 protein of interest.

The amino acid sequence of the cytochrome P450 protein of the present invention preferably has a sequence identity of 70% or more, 80% or more, 85% or more, 90% or more, 95% or more, 97% or more, 98% or more, or 99% or more to the wild-type amino acid sequence, such as the amino acid sequence of SEQ ID NO: 1, 2, 3, or 4. It is well known in the art that a modified protein having at least a certain level of amino acid sequence identity to the corresponding unmodified protein will have a high possibility of having a similar level of activity and substrate specificity to that of the unmodified protein. Alternatively, the amino acid sequence of the cytochrome P450 protein of the present invention may have a sequence identity of 70% or more, 80% or more, 85% or more, 90% or more, 95% or more, 97% or more, 98% or more, or 99% or more to the amino acid sequence of other cytochrome P450 proteins belonging to a certain family or subfamily to which the wild-type cytochrome P450 capable of oxidizing the methylene group at position 3 of α-guaiene belongs.

Even with a relatively low sequence identity, conservatively modified amino acid sequences will tend to maintain activity similar to that of the unmodified amino acid sequences. When conservatively modified, therefore, the amino acid sequence of the cytochrome P450 protein of the present invention may have a sequence identity of 60% or more, 70% or more, 80% or more, 85% or more, or 90% or more to the wild-type amino acid sequence, such as the amino acid sequence of SEQ ID NO: 1, 2, 3, or 4.

The amino acid sequence identity can be determined by methods known in the art. Specific examples of such methods include calculation methods using default parameters and identity search software, e.g., FASTA, BLAST, BLASTX, or Smith-Waterman (Meth. Enzym., 164, 765 (1988)).

The cytochrome P450 protein of the present invention may have any level of the oxidation activity. For example, the cytochrome P450 protein of the present invention may have 5% or more, 10% or more, 30% or more, 50% or more, 70% or more, 90% or more, 100% or more, 120% or more, or 150% or more of the oxidation activity of any of the cytochrome P450 proteins shown in the EXAMPLES section. The level of the oxidation activity may be determined by any method. For example, the level of the oxidation activity can be determined by comparing the yield of rotundone as a biological conversion product with that in the case where a specific cytochrome P450 protein shown in the EXAMPLES section is used.

<DNA Encoding Cytochrome P450>

The cytochrome P450-encoding DNA of the present invention (hereinafter also referred to as the cytochrome P450 gene of the present invention) encodes a protein capable of oxidizing the methylene group at position 3 of α-guaiene. The cytochrome P450 gene of the present invention may have any nucleotide sequence as long as it encodes such a protein.

For example, the nucleotide sequence of the cytochrome P450 gene of the present invention may be identical to or include a nucleotide sequence encoding a wild-type cytochrome P450 protein capable of oxidizing the methylene group at position 3 of α-guaiene. Examples of genes encoding wild-type cytochrome P450 proteins include, but are not limited to, the gene encoding CYP152A1 (gene name cypC or ybdT, GenBank Accession No. AL009126.3) (SEQ ID NO: 5), the gene encoding CYP107K1 (gene name pksS, GenBank Accession No. EF546698.1) (SEQ ID NO: 6), the gene encoding CYP106 (BCE_2659) (locus tag BCE_2659 of GenBank Accession No. AE017194.1) (SEQ ID NO: 7), and the gene encoding CYP107 (BCE_2696) (gene name cypA, locus tag BCE_2696 of GenBank Accession No. AE017194.1) (SEQ ID NO: 8).

The nucleotide sequence of the cytochrome P450 gene of the present invention may include a sequence derived by any modification (substitution, deletion, addition, insertion, or other gene editing processes) of the wild-type nucleotide sequence, as long as it does not lose the oxidation activity. The modification without losing the oxidation activity may have any effect; the modification may change as desired, specifically, increase or decrease the oxidation activity.

At least one or any number of nucleotides may be modified. For example, the number of modified nucleotides is 30 or less, 20 or less, 15 or less, 10 or less, or at most several.

Examples of the nucleotide modification include, but are not limited to, conservative mutations. In this context, "conservative mutations" means modifications that change a codon to one that encodes the same amino acid or a different amino acid having similar physical, chemical, and/or structural properties (namely, the conservative amino acid substitutions described above).

Alternatively, the cytochrome P450 gene of the present invention may encode a protein capable of oxidizing the methylene group at position 3 of α-guaiene and having an amino acid sequence derived by modifying one or more amino acids in the amino acid sequence of a wild-type cytochrome P450 protein. Such a modified gene may be, for example, a DNA encoding a protein having an amino acid sequence derived by deletion, substitution, or addition of at least one amino acid or one to several amino acids in the amino acid sequence of any one of SEQ ID NOS: 1 to 4, a DNA encoding a protein having an amino acid sequence having a sequence identity of 70% or more, 80% or more, 85% or more, 90% or more, 95% or more, or 98% or more to the amino acid sequence of any one of SEQ ID NOS: 1 to 4, or a DNA encoding a protein having an amino acid sequence derived by conservative substitution of one or more amino acids in the amino acid sequence of anyone of SEQ ID NOS: 1 to 4 and having a sequence identity of 60% or more, 70% or more, 80% or more, 85% or more, or 90% or more to the amino acid sequence of any one of SEQ ID NOS: 1 to 4.

Conventionally known techniques may be used to produce the DNA having a nucleotide sequence encoding an amino acid sequence derived by deletion, substitution, or addition of one or more amino acids or to produce a DNA having a nucleotide sequence different from the nucleotide sequences of SEQ ID NOS: 5 to 8. For example, the substitution of a specific nucleotide or nucleotides can be performed using site-directed mutagenesis techniques. Site-directed mutagenesis techniques include, for example, T. Kunkel site-directed mutagenesis (Kunkel, T. A. Proc. Nati. Acad. Sci. U.S.A. 82, pp. 488-492 (1985)) and gapped duplex method. Mutations may also be introduced using a mutation-introducing kit based on site-directed mutagenesis (e.g., Mutan-K (manufactured by TAKARA SHUZO CO., LTD.), Mutan-G (manufactured by TAKARA SHUZO CO., LTD.), or LA PCR in vitro Mutagenesis Series Kit manufactured by manufactured by TAKARA SHUZO CO., LTD.).

The present invention also encompasses a DNA hybridizable under stringent conditions with a DNA having a nucleotide sequence complementary to the nucleotide sequence of the wild-type nucleotide sequence, such as any one of those of SEQ ID NOS: 5 to 8.

As used herein, the term "stringent conditions" means conditions where hybridization occurs between a certain DNA and any other DNA with at least a certain level of sequence identity but does not occur between the certain DNA and any other DNA with a low sequence identity. More specifically, the term "stringent conditions" means that after the hybridization, the membrane is washed in a high-temperature, low-salt-concentration solution.

For example, Molecular Cloning, A Laboratory Manual, Second Edition, Cold Spring Harbor Laboratory Press, (1989); Current Protocols in Molecular Biology, John Wiley & Sons, 1987-1997; DNA Cloning 1: Core Techniques, A Practical Approach, Second Edition, Oxford University (1995), and other texts can be referred to for details of hybridization methods and "stringent conditions."

Herein, "stringent conditions," which are nucleotide sequence dependent, are not limited to specific values. For example, stringent conditions may be such that dissociation from the DNA will not occur after a process including heating in a solution of 6×SSC (standard saline citrate, 1×SSC includes 0.15 M of NaCl and 0.015 M of sodium citrate), 0.5% SDS, and 50% formamide at 42° C. overnight and then washing in a solution of 0.1×SSC and 0.5% SDS at 68° C. for 30 minutes or after a process including hybridization in a solution of 6×SSC and 40% formamide at 25° C. and then washing in a solution of 1×SSC at 55° C. More specifically, for example, the conditions during the hybridization may be such that the sodium salt concentration is 15 to 750 mM, preferably 15 to 500 mM, more preferably 15 to 300 mM or 15 to 200 mM, the temperature is 25 to 70° C., preferably 50 to 70° C., more preferably 55 to 68° C., and/or the formamide concentration is 0 to 50%, preferably 20 to 50%, more preferably 35 to 45%. The conditions for filter washing after the hybridization under stringent conditions may be such that the sodium salt concentration is 15 to 750 mM, preferably 15 to 500 mM, more preferably 15 to 300 mM or 15 to 200 mM, and/or the temperature is 50 to 70° C., preferably 55 to 70° C., more preferably 60 to 65° C. Although the stringency depends on conditions, such as salt concentration, formamide concentration, and temperature, it is obvious for those skilled in the art that these conditions can be selected so that the desired stringency can be obtained.

A DNA hybridizable under such stringency conditions will have a sequence identity as high as 80% or more, 85% or more, 90% or more, 95% or more, 98% or more, or 99% or more to the nucleotide sequence of the template DNA, and a protein encoded by the DNA having a nucleotide sequence with such a level of sequence identity may have activity similar to that of the protein encoded by the template DNA.

The cytochrome P450 gene of the present invention may also be cDNA or may have a nucleotide sequence before splicing, in other words, may have a nucleotide sequence corresponding to an intron-containing mRNA precursor. This is because a genome nucleotide sequence corresponding to the nucleotide sequence of such a mRNA precursor can provide a sequence substantially the same as the DNA of the present invention through the splicing reaction after the transcription and because a protein encoded by such a sequence could have substantially the same activity as the cytochrome P450 protein having the amino acid sequence of any one of SEQ ID NOS: 1 to 4 (see the EXAMPLES section). For example, the DNA may be such that it can produce a mature mRNA having the nucleotide sequence of any one of SEQ ID NOS: 5 to 8 after splicing.

<Electron Transfer Protein>

In the context of the present invention, the term "electron transfer protein" means a protein that is capable of receiving electrons from NAD(P)H and transferring the electrons to the cytochrome P450 protein of the present invention (hereinafter this activity will also be simply referred to as "electron transfer activity"). Examples of the electron transfer protein include ferredoxin (Fdx) and ferredoxin reductase (FdR), cytochrome P450 reductase (CPR), pyruvate ferredoxin oxidoreductase (PFOR), oxoacid ferredoxin oxidoreductase (OFOR), and fragments thereof capable of transferring electrons to the cytochrome P450 protein of the present invention. Alternatively, an electron transfer activity-possessing fragment of the self-sufficient cytochrome P450 mentioned above may also be used (e.g., a reducing fragment of the CYP102 family protein shown above or a reducing domain of cytochrome P450RhF shown in Nodate et al. described above).

In particular, ferredoxin and ferredoxin reductase are known as a combination of proteins capable of transferring electrons to bacteria-derived cytochrome P450 (hereinafter, this combination will also be referred to as "redox partner proteins") and reported to transfer electrons to various cytochrome P450 proteins (Hannemann et at., (2007) Biochimica et Biophysica Acta, 1770, pp. 330-344). These reported redox partner proteins may also be used in the present invention.

Any types of ferredoxin and ferredoxin reductase may be used. Ferredoxin and ferredoxin reductase may be derived from any organism as long as they are capable of transfer electrons to the cytochrome P450 protein of the present invention. For example, PIR, UniProt, and other data bases may be used to search and identify the amino acid sequences of ferredoxin and ferredoxin reductase derived from various biological species.

Examples of ferredoxin that can be used in the present invention include, but are not limited to, spinach-derived ferredoxin, *Pseudomonas putida*-derived putidaredoxin, animal-derived adrenodoxin, *Sphingomonas subterranea*-derived ferredoxin, *Novosphingobium aromaticivorans*-derived ferredoxin, *Escherichia coli*-derived flavodoxin and ferredoxin, *Saccharomyces cerevisiae*-derived ferredoxin, *Acinetobacter* bacteria-derived ferredoxin, or various other ferredoxin-like proteins.

Examples of ferredoxin reductase that can be used in the present invention include, but are not limited to, spinach-derived ferredoxin reductase, *Pseudomonas putida*-derived putidaredoxin reductase, animal-derived adrenodoxin reductase, *Sphingomonas subterranea*-derived ferredoxin reductase, *Novosphingobium aromaticivorans*-derived ferredoxin reductase, *Escherichia coli*-derived flavodoxin reductase and ferredoxin reductase, *Saccharomyces cerevisiae*-derived ferredoxin reductase, and *Acinetobacter* bacteria-derived ferredoxin reductase.

Preferred examples of wild-type electron transfer proteins that can be used in the present invention also include, but are not limited to, a type of ferredoxin and ferredoxin reductase, such as a protein encoded by the *Acinetobacter* aciBC gene (GenBank Accession No. CP012952.1), and a combination of putidaredoxin (GenBank Accession No. AAA25759.1) (SEQ NO: 10) and putidaredoxin reductase (GenBank Accession No. AAA25758.1) (SEQ NO: 11).

Ferredoxin and ferredoxin reductase may be derived from the same or different organisms. In addition, ferredoxin and ferredoxin reductase may each be homologous or heterologous to the cytochrome P450. There are known heterogeneous redox partner proteins capable of transferring electrons to cytochrome P450 (see, e.g., Arisawa, XB119, SCEJ 75th Annual Meeting (Kagoshima, 2010); Agematu et al., (2006) Biosci. Biotechnol. Biochem. 70, pp. 307-311).

Ferredoxin and ferredoxin reductase may also be commercially available products, such as those available from Sigma-Aldrich Co. (Catalog Nos. F3013 and F0628).

As mentioned above, a fusion of a cytochrome P450 protein with an electron transfer protein may be prepared and then allowed to act on α-guaiene to convert α-guaiene to rotundone. The literatures on the fusion mentioned above may be referred to for the preparation of the fusion.

The amino acid sequence of the electron transfer protein of the present invention may be identical to or include the amino acid sequence of any of the above wild-type electron transfer proteins, such as those of SEQ ID NOS: 10 and 11, or may be identical to or include a sequence derived by partially modifying the amino acid sequence of the wild-type electron transfer proteins. The mutation may have any effect; the mutation may change as desired, specifically, increase or decrease the electron transfer activity.

At least one or any number of amino acids may be modified. For example, the number of modified amino acids is 30 or less, 20 or less, 15 or less, 10 or less, or at most several. The amino acid modification may be, for example, the conservative substitution described above.

Like the cytochrome P450 protein of the present invention, the electron transfer protein of the present invention may be an artificially biosynthesized product or a product by synthesized by chemical protein synthesis techniques.

The terms "several," "sequence identity," and "conservative substitution" are as defined above.

As mentioned above, some cytochrome P450 proteins do not require NAD(P)H and any electron transfer protein to exhibit monooxygenase activity. Therefore, the electron transfer protein is not essential in the present invention. Examples of such cytochrome P450 proteins include CYP74A shown above and cytochrome P450 proteins belonging to the CYP152 family, such as CYP152A1, CYP152B1, and CYP152L1, which use hydrogen peroxide.

<DNA Encoding Electron Transfer Protein>

In the present invention, the electron transfer protein-encoding DNA is a DNA that encodes an electron transfer protein having the electron transfer activity described above (hereinafter also referred to as the electron transfer protein gene of the present invention). The DNA may have any nucleotide sequence as long as it encodes such an electron transfer protein.

Preferred examples include, but are not limited to, DNAs encoding Fdx and FdR and DNAs encoding their fragments capable of transferring electrons to the cytochrome P450 protein of the present invention. Data bases storing gene information, such as DDBJ/EMBL/GenBank International Nucleotide Sequence Database, may be used to identify employable nucleotide sequences of ferredoxin and ferredoxin reductase derived from various biological species.

Non-limiting examples of wild-type electron transfer protein genes include, but are not limited to, the genes encoding putidaredoxin and putidaredoxin reductase shown above (gene names camA and camB, GenBank Accession No. J05406.1) (SEQ ID NO: 9).

The electron transfer protein-encoding DNA may also have a nucleotide sequence derived by modifying at least one nucleotide or one to several nucleotides in the nucleotide sequence of a wild-type electron transfer protein gene, such as the nucleotide sequence of SEQ ID NO: 9, or have a nucleotide sequence having a sequence identity of 70% or more, 80% or more, 85% or more, 90% or more, 95% or more, or 98% or more to the nucleotide sequence of the wild-type electron transfer protein gene, as long as it does not lose the electron transfer activity.

Examples of the nucleotide modification include, but are not limited to, conservative mutations.

The present invention also encompasses a DNA encoding a protein that is capable of transferring electrons to the cytochrome P450 protein of the present invention and has an amino acid sequence derived by modifying one or more amino acids in the amino acid sequence of a wild-type electron transfer protein. Such a modified DNA may be, for example, a DNA encoding a protein having an amino acid sequence derived by deletion, substitution, or addition of at least one amino acid or one to several amino acids in the amino acid sequence of SEQ ID NOS: 10 and 11, a DNA encoding a protein having an amino acid sequence having a sequence identity of 60% or more, 70% or more, 80% or more, 85% or more, 90% or more, 95% or more, or 98% or more to the amino acid sequence of SEQ ID NOS: 10 and 11, or a DNA encoding a protein having an amino acid sequence derived by conservative substitution of one or more amino acids in the amino acid sequence of SEQ ID NOS: 10 and 11 and having a sequence identity of 60% or more, 70% or more, 80% or more, 85% or more, or 90% or more to the amino acid sequence of SEQ ID NOS: 10 and 11.

Conventionally known techniques may be used to produce the DNA having a nucleotide sequence encoding an amino acid sequence derived by deletion, substitution, or addition of one or more amino acids or to produce a DNA having a base sequence different from the base sequence of SEQ ID NO: 9. For example, the substitution of a specific nucleotide or nucleotides can be performed using site-directed mutagenesis techniques.

The present invention also encompasses a DNA hybridizable under stringent conditions with a DNA having a nucleotide sequence complementary to the base sequence of the wild-type base sequence, such as the nucleotide sequence of SEQ ID NO: 9.

Like the cytochrome P450 gene of the present invention, the electron transfer protein gene may also be cDNA or may have a nucleotide sequence before splicing, in other words, a nucleotide sequence corresponding to an intron-containing mRNA precursor. For example, the DNA may be such that it can produce a mature mRNA having the base sequence of SEQ ID NO: 9 after splicing.

The terms "several," "sequence identity," "conservative mutation," and "stringent conditions" are as defined above.

<<Method of Converting α-Guaiene to Rotundone>>

In the method of the present invention, the cytochrome P450 protein of the present invention is allowed to act on α-guaiene to produce rotundone. In the method of the present invention, a purified cytochrome P450 protein of the present invention may be allowed to act on α-guaiene to oxidize the methylene group at position 3 of α-guaiene to carbonyl group. Alternatively, an organism, cells, or a fragment or homogenate obtained therefrom, in which the cytochrome P450 protein of the present invention is produced, may be mixed with α-guaiene so that the cytochrome P450 protein of the present invention is allowed to act on α-guaiene to oxidize the methylene group at position 3 of α-guaiene to the carbonyl group. The conditions for such action may be determined based on those commonly used in methods for converting certain substrates to biological conversion products using organisms, cells, isolated cells or preparations (fragments or homogenates) obtained therefrom having an enzyme activity of interest. For example, the present invention may use living cells (or living bacterial cells) that produce a cytochrome P450 protein capable of oxidizing the methylene group at position 3 of α-guaiene and optionally produce a protein capable of transferring electrons to the cytochrome P450 protein, or may use living cells (or living bacterial cells) that carry these proteins. In such cases, under the conditions for such action, the cells and optionally other materials may be incubated in the presence of the substrate α-guaiene in a culture medium in an environment with no adverse effect on the cells or other materials, for example, at a physiological temperature, for a certain period of time. On the other hand, the present invention may use a reaction system containing a cytochrome P450 protein capable of oxidizing the methylene group at position 3 of α-guaiene and optionally containing a protein preparation (which may also be a purified protein) including a protein capable of transferring electrons to the cytochrome P450 protein, or may use isolated cells or a preparation (cell fragments or homogenate) containing such a protein or proteins. In such cases, under the conditions for such action, the protein or proteins may be mixed or allowed to coexist with the substrate α-guaiene in an aqueous solution, buffered with a physiologically acceptable buffer if needed, and incubated at, for example, room temperature, for a certain period of time. If necessary, the incubation time may be determined with reference to, for example, the amount of rotundone converted from α-guaiene. The amount of rotundone can be determined by sampling an aliquot of the reaction mixture over time and subjecting the aliquot to the quantification method described below. The rotundone produced in this way may be purified or isolated from the reaction mixture by methods known per se, such as extraction, distillation, chromatography, crystallization, and partition extraction.

Hereinafter, specific examples of the cases will be described.

<Cases of Using Organisms or Cells>

The organism or cell that produces the cytochrome P450 protein of the present invention may be of any type capable of expressing the cytochrome P450 gene of the present invention, such as an organism or cell that inherently produces the cytochrome P450 protein of the present invention or an organism or cell obtained by modifying an original organism or cell not capable of producing the protein using genetic modification techniques to give it an ability to produce the cytochrome P450 protein (hereinafter also referred to as the recombinant of the present invention). Examples include, but are not limited to, bacteria (*E. coli*, lactic bacteria, actinomycete, *Bacillus subtilis*), yeasts, fungi, plants, plant cells, animal cells, and insect cells.

The recombinant of the present invention may be prepared by any methods. For example, the recombinant of the present invention may be prepared by a process that includes expressibly inserting the cytochrome P450 gene of the present invention and/or the electron transfer protein gene of the present invention into a certain vector to produce a vector (hereinafter also referred to as the recombinant vector of the present invention) and then introducing the vector into an organism or cells. At least one gene copy or any number of gene copies may be inserted into the vector. The cytochrome P450 gene of the present invention and the electron transfer protein gene of the present invention may be inserted into the same vector to be introduced into an organism or cells, or may be inserted into different vectors to be independently introduced into an organism or cells.

The vector may be of any type. The type of the vector may be selected as appropriate depending on the purpose (e.g., cloning or gene expression) or the host into which the vector is to be introduced (e.g., *E. coli*, yeast, insect cells, animal cells, plant cells, or plants, particularly leguminous plants). Examples of usable vectors include, but are not limited to, plasmid vectors, such as pBI vectors, pPZP vectors, pSMA vectors, pUC vectors, pBR vectors, pBluescript vectors (Stratagene), and pTriEX™ vectors (TaKaRa); other types of vectors, such as cauliflower mosaic virus (CaMV) vectors, bean golden mosaic virus (BGMV) vectors, and tobacco mosaic virus (TMV) vectors; and binary vectors, such as pBI vectors, which may be of an autonomous replication type or an chromosome integration type.

Methods known in the art can be used to expressibly insert the DNA of interest into the vector. Methods generally used include cleaving a purified DNA or a fragment thereof with suitable restriction enzymes and then inserting the product into the corresponding restriction enzyme site or multi-cloning site of any suitable one of the vectors shown above. Specific methods are described in, for example, Sambrook, J. et. al., (1989) Molecular Cloning: a Laboratory Manual Second Ed., Cold Spring Harbor Laboratory Press, Cold Spring Harbor, N.Y.

Examples of methods for vector introduction include *Agrobacterium* methods, PEG-potassium phosphate methods, electroporation methods, liposome methods, particle gun methods, and microinjection methods. When introduced with the vector into a host, the DNA may be incorporated in the genome DNA of the host or may exist as it is (e.g., as it is contained in the vector). The introduced DNA may stay retained in the host cell, for example, as in a case where it is incorporated in the genome DNA of the host, or may be transiently retained.

The introduction of the gene of the present invention can be checked by methods known in the art, such as PCR methods, Southern hybridization methods, Northern hybridization methods, or in situ hybridization methods.

The recombinant vector of the present invention may contain any appropriate element in addition to the gene of the present invention. For example, a regulatory region, such as a promoter, an enhancer, or a terminator, or other genes, e.g., a selectable marker gene and/or a J-amyrin synthase gene, may be linked to the vector. The type of the promoter, enhancer, terminator, or selectable marker may be selected as appropriate depending on the purpose (e.g., cloning, gene expression, or screening) or the host into which the DNA is to be introduced (e.g., bacteria, yeasts, insect cells, animal cells, plant cells, or plants).

The selectable marker gene may be of any type capable of distinguishing the vector-carrying cells from cells not carrying the vector. General examples of the selectable marker gene include drug resistance genes (e.g., tetracycline resistance genes, ampicillin resistance genes, kanamycin resistance genes, hygromycin resistance genes, spectinomycin resistance genes, chloramphenicol resistance genes, neomycin resistance genes), fluorescence or luminescence reporter genes (e.g., luciferase, β-galactosidase, β-glucuronidase (GUS), green fluorescence protein (GFP)), and enzyme genes, e.g., neomycin phosphotransferase II (NPT H) and dihydrofolate reductase genes. A gene that can enable the production of an essential nutrient may also be introduced, and the resulting cells may be cultured in a medium free of the essential nutrient, so that the grown cells can be obtained as the recombinant of the present invention.

The recombinant vector of the present invention prepared as described above can be introduced into a suitable host for use in conversion of α-guaiene to (−)-rotundone with high efficiency and high purity.

When the recombinant capable of expressing the cytochrome P450 protein of the present invention is allowed to act on α-guaiene to convert it to (−)-rotundone, any culture media suitable for the host may be used as the culture media for the recombinant. Such culture media may be those known in the art. For example, LB or M9 media are generally used when the host to be cultured is a bacterium, such as *E. coli*, and YPD, YPG, YPM, YPDM, or SMM media are generally used when the host to be cultured is a yeast. The culture media may contain, as needed, a carbon source (e.g., glucose, glycerin, mannitol, fructose, lactose), a nitrogen source (e.g., an inorganic nitrogen source such as ammonium sulfate or ammonium chloride, an organic nitrogen source such as a casein degradation product, a yeast extract, polypeptone, bactotryptone, or a beef extract), an inorganic salt (e.g., sodium diphosphate, potassium diphosphate, magnesium chloride, magnesium sulfate, calcium chloride), a vitamin (e.g., vitamin B1), and a drug (an antibiotic, such as ampicillin, tetracycline, or kanamycin) as appropriate. The culture media may also contain α-guaiene as a substrate for the cytochrome P450 protein of the present invention. The culture media may further contain any oxidizing agent (e.g., dimethyl sulfoxide (DMSO)) and an expression inducing agent (e.g., isopropyl-β-D-thiogalactopyranoside (IPTG)).

Any culture conditions may be used as long as the cultivation under the conditions allows expression of each gene used in the present invention and/or expression of the activity of the cytochrome P450 protein of the present invention. In general, the cultivation is performed at 10 to 45° C. for several hours to several hundred hours optionally with ventilation and stirring until any desired OD is attained. More specific conditions may be determined with reference to, for example, Sambrook, J. et. al., (1989) Molecular Cloning: a Laboratory Manual Second Ed., Cold Spring Harbor Laboratory Press, Cold Spring Harbor, N.Y.

The cytochrome P450 protein of the present invention can be collected from cultures (including culture supernatants and/or cultured recombinants) by extracting the cytochrome P450 protein of the present invention from cultures using known methods and purifying the extract as needed. For example, solvent extraction, salting out, solvent precipitation, dialysis, ultrafiltration, gel electrophoresis, gel filtration chromatography, ion-exchange chromatography, reversed-phase chromatography, affinity chromatography, and other methods may be used alone or in any combination for the attainment of the cytochrome P450 protein of interest.

The recombinant of the present invention and α-guaiene may be added to the culture system described above, and the recombinant may be cultured in the resulting system, so that rotundone can be produced with high efficiency and high purity. Such a culture system is a new system capable of converting α-guaiene to rotundone with high efficiency and high purity.

In the case of allowing the purified cytochrome P450 protein of the present invention to act on α-guaiene, any reaction system that allows the purified cytochrome P450 protein to exhibit the activity to oxidize the methylene group at position 3 of α-guaiene may be used. For example, a cytochrome P450 reconstituted system may be used (e.g., a system including the purified cytochrome P450 protein of the present invention, an oxidizing agent, and a substrate or a system further including an electron transfer protein in addition to them). Such a reconstituted system can be prepared with reference to, for example, Furuya et al., (2008) Chem. Biol., 15, pp. 563-572. Such a reconstituted system is a new system capable of converting α-guaiene to rotundone with high efficiency and high purity.

Whether rotundone is produced as an α-guaiene conversion product can be determined by any known method, such as chromatography. Specifically, for example, the retention time and MS spectrum of an α-guaiene conversion product may be obtained by GC/MS and compared with those of a rotundone standard. If they agree with those of the rotundone standard, the conversion product can be identified as rotundone.

<<Screening Method>>

The present invention also provides a method of screening proteins presumed to have an ability to convert α-guaiene to (−)-rotundone to identify a protein having the ability. This method of the present invention includes, in order, the steps of: allowing a certain protein to act on α-guaiene or allowing a certain protein to act on α-guaiene in the presence of an electron transfer protein capable of transferring electrons to the certain protein; and detecting rotundone. Any protein presumed to have the ability to convert α-guaiene to (−)-rotundone may be subjected to the screening method. Examples of such a protein include proteins that have an amino acid sequence having a sequence identity of 40% or more, 50% or more, 55% or more, 60% or more, 70% or more, 80% or more, or 90% or more to the amino acid sequence of any one of CYP152A1, CYP107K1, CYP106 (BCE_2659), and CYP107 (BCE_2696) shown in the EXAMPLES section, and proteins belonging to cytochrome P450. The electron transfer protein is typically, but not limited to, a combination of ferredoxin and ferredoxin reductase. This method makes it possible to screen proteins to identify new proteins capable of converting α-guaiene to rotundone.

The present invention also provides a method of screening proteins presumed to have an ability to transfer electrons to a cytochrome P450 protein capable of converting α-guaiene to rotundone to identify a protein having the electron transfer activity. This method of the present invention includes, in order, the steps of: allowing a certain protein to act on α-guaiene in the presence of a cytochrome P450 protein capable of converting α-guaiene to rotundone, specifically at least one cytochrome P450 protein selected from CYP152A1, CYP107K1, CYP106 (BCE_2659), and CYP107 (BCE_2696) or a their analogue capable of oxidizing the methylene at position 3 of α-guaiene; and detecting rotundone. Any protein presumed to have the electron transfer activity may be subjected to the screening. Examples of such a protein include proteins that have an amino acid sequence having a sequence identity of 40% or more, 50% or more, 55% or more, 60% or more, 70% or more, 80% or more, or 90% or more to the amino acid sequence of ferredoxin and ferredoxin reductase or the amino acid sequence of putidaredoxin and putidaredoxin reductase (SEQ ID NOS: 10 and 11). Examples of the cytochrome P450 analogue include, but are not limited to, at least one selected from those recited in the Cytochrome P450 Protein section. This method makes it possible to screen proteins to identify new electron transfer proteins capable of transferring electrons to the cytochrome P450 protein of the present invention.

<<Enzyme Activity Measuring Method>>

The present invention also provides a method of measuring the activity of a certain protein to convert α-guaiene to rotundone. The method of the present invention includes, in order, the steps of: allowing a certain protein to act on α-guaiene or allowing a certain protein to act on α-guaiene in the presence of an electron transfer protein capable of transferring electrons to the certain protein; and detecting rotundone. Any protein may be subjected to this measurement. Examples include proteins having a sequence identity of 40% or more, 50% or more, 55% or more, 60% or more, 70% or more, 80% or more, or 90% or more to the amino acid sequence of CYP152A1, CYP107K1, CYP106 (BCE_2659), or CYP107 (BCE_2696), and proteins belonging to cytochrome P450. Any electron transfer protein may also be used, such as a combination of ferredoxin and ferredoxin reductase. This method makes it possible to search for and identify cytochrome P450 proteins having a desired intensity of the oxidation activity.

<<Uses of Rotundone>>

The rotundone produced by the method of the present invention may be directly added in any amount to beverages and foods so that it can enhance flavors, e.g., fruit flavors, specifically freshness and fruitiness. The rotundone may also be mixed with other ingredients to prepare an aroma composition, which may be used to enhance, for example, fruit flavors, specifically freshness and fruitiness, of beverages and foods. Examples of other aroma ingredients that can be mixed with rotundone to prepare the aroma composition include a variety of synthetic aroma compounds, natural aroma compounds, natural essential oils, and animal and plant extracts.

Examples of other aroma ingredients also include the synthetic aroma compounds, natural aroma compounds, natural essential oils, and animal and plant extracts listed in Tokkyo Cho, Shuchi Kanyo Gijutsushu (Koryo) II Bu Shokuhin Koryo (Japan Patent Office, Well-Known Conventional Techniques Collection (Flavors), Part II, Food Flavors), pp. 8-87, published on Jan. 14, 2000.

If necessary, the aroma composition including rotundone of the present invention as an active ingredient may contain a solvent, e.g., water or ethanol, and a flavor retention agent, e.g., ethylene glycol, 1,2-propylene glycol, glycerin, benzyl benzoate, triethyl citrate, Hercolyn, fatty acid triglyceride, or fatty acid diglyceride, which are generally used in aroma compositions.

An emulsified aroma composition may also be prepared by mixing an emulsifier, e.g., glycerin fatty acid ester, sorbitan fatty acid ester, propylene glycol fatty acid ester, sucrose fatty acid ester, lecithin, *Quillaja saponaria* saponin, or sodium caseinate, with the aroma composition including rotundone as an active ingredient. A powdered flavor composition may also be prepared by mixing, for example, Arabian gum or dextrin with the flavor composition including rotundone as an active ingredient and then drying the mixture.

The aroma composition including rotundone produced by the method of the present invention may be added alone in any amount to a variety of beverages and foods as mentioned above, or any aroma formulation that contains the aroma composition including rotundone produced by the method of the present invention may be added in any amount to a variety of beverages and foods.

Specific examples of beverages and foods containing rotundone produced by the method of the present invention include, but are not limited to, carbonated drinks, fruit juice drinks, soft drinks, luxury drinks, alcoholic drinks, dairy products, desserts and mixes for production thereof, confectionaries and mixes for production thereof, breads, soups, various convenience foods, and other general food products, and oral compositions such as dentifrices.

The content of rotundone produced by the method of the present invention in the aroma composition may vary with other flavor ingredients mixed therewith. In general, the content of rotundone produced by the method of the present invention in the aroma composition may be in the range of 0.5 ppt to 0.5 ppm, preferably 1 ppt to 0.2 ppm, based on the weight of the aroma composition.

When rotundone is added to enhance fruit flavors, specifically freshness and fruitiness, the content of rotundone in the various products mentioned above may vary with the type or form of the products. In general, the content of rotundone in the product may be in the range of 0.005 ppt to 5 ppt, preferably 0.01 ppt to 2 ppt, based on the weight of the product.

In light of the above descriptions, the present invention may also provide the followings.

For example, the present invention may also provide method of producing (−)-rotundone from α-guaiene, the method including the following steps (1) and/or (2): (1) allowing a cytochrome P450 protein to act on α-guaiene, which cytochrome P450 protein belongs to a CYP152 family and is capable of oxidizing the methylene group at position 3 of α-guaiene to the carbonyl group; (2) allowing a cytochrome P450 protein to act on α-guaiene in the presence of an electron transfer protein capable of transferring electrons to the cytochrome P450 protein, which cytochrome P450 protein belongs to a CYP152, CYP106, or CYP107 family and is capable of oxidizing the methylene group at position 3 of α-guaiene to the carbonyl group, wherein the cytochrome P450 protein in the step (1) is at least one selected from (a), (b), and (c), and the cytochrome P450 protein in the step (2) is at least one selected from (a), (b), (c), (d), (e), and (f), wherein (a), (b), (c), (d), (e), and (f) are as follows:
 (a) a protein having an amino acid sequence of SEQ ID NO: 1;
 (b) a protein that has an amino acid sequence having a sequence identity of at least 90% to an amino acid sequence of SEQ ID NO: 1;
 (c) a protein that has an amino acid sequence including a conservative substitution of at least one amino acid of an amino acid sequence of SEQ ID NO: 1 and having a sequence identity of at least 80% to the amino acid sequence of SEQ ID NO: 1;
 (d) a protein having an amino acid sequence of any one of SEQ ID NOS: 2 to 4;
 (e) a protein that has an amino acid sequence having a sequence identity of at least 90% to an amino acid sequence of any one of SEQ ID NOS: 2 to 4;
 (f) a protein that has an amino acid sequence including a conservative substitution of at least one amino acid of an amino acid sequence of any one of SEQ ID NOS: 2 to 4 and having a sequence identity of at least 80% to the amino acid sequence of any one of SEQ ID NOS: 2 to 4.

In certain embodiments, the cytochrome P450 protein in the step (1) is *Bacillus subtilis*-derived CYP152A1, and the cytochrome P450 protein in the step (2) is at least one selected from the group consisting of *Bacillus subtilis*-derived CYP152A1 and CYP107K1, and *Bacillus cereus*-derived CYP106 (BCE_2659) and CYP107 (BCE_2696).

In certain embodiments, the electron transfer protein is a combination of ferredoxin and ferredoxin reductase.

In certain embodiments, the electron transfer protein is a combination of at least one selected from (A), (B), and (C) and at least one selected from (D), (E), and (F), wherein (A), (B), (C), (D), (E), and (F) are as follows:
 (A) a protein having an amino acid sequence of SEQ ID NO: 10;
 (B) a protein that has an amino acid sequence having a sequence identity of at least 90% to an amino acid sequence of SEQ ID NO: 10;
 (C) a protein that has an amino acid sequence including a conservative substitution of at least one amino acid of an amino acid sequence of SEQ ID NO: 10 and having a sequence identity of at least 80% to the amino acid sequence of SEQ ID NO: 10;
 (D) a protein having an amino acid sequence of SEQ ID NO: 11;
 (E) a protein that has an amino acid sequence having a sequence identity of at least 90% to an amino acid sequence of SEQ ID NO: 11;
 (F) a protein that has an amino acid sequence including a conservative substitution of at least one amino acid of an amino acid sequence of SEQ ID NO: 11 and having a sequence identity of at least 80% to the amino acid sequence of SEQ ID NO: 11.

In certain embodiments, the method of the present invention further includes producing the cytochrome P450 protein for the step (1) by expressing at least one DNA selected from (g), (h), (i), (j), and (k); and/or producing the cytochrome P450 protein for the step (2) by expressing at least one DNA selected from (g), (h), (i), (j), (k), (l), (m), (n), (o), and (p), wherein (g), (h), (i), (j), (k), (l), (m), (n), (o), and (p) are as follows:
 (g) a DNA having a nucleotide sequence of SEQ ID NO: 5;
 (h) a DNA that has a nucleotide sequence having a sequence identity of at least 90% to a nucleotide sequence of SEQ ID NO: 5;
 (i) a DNA hybridizable, under stringent conditions, with a DNA having a nucleotide sequence complementary to a nucleotide sequence of SEQ ID NO: 5;
 (j) a DNA encoding a protein that has an amino acid sequence having a sequence identity of at least 90% to an amino acid sequence of SEQ ID NO: 1;
 (k) a DNA encoding a protein that has an amino acid sequence including a conservative substitution of at least one amino acid of an amino acid sequence of SEQ ID NO: 1 and having a sequence identity of at least 80% to the amino acid sequence of SEQ ID NO: 1;
 (l) a DNA having a nucleotide sequence of any one of SEQ ID NOS: 6 to 8;

(m) a DNA that has a nucleotide sequence having a sequence identity of at least 90% to a nucleotide sequence of any one of SEQ ID NOS: 6 to 8;

(n) a DNA hybridizable, under stringent conditions, with a DNA having a nucleotide sequence complementary to a nucleotide sequence of any one of SEQ ID NOS: 6 to 8;

(o) a DNA encoding a protein that has an amino acid sequence having a sequence identity of at least 90% to an amino acid sequence of any one of SEQ ID NOS: 2 to 4;

(p) a DNA encoding a protein that has an amino acid sequence including a conservative substitution of at least one amino acid of an amino acid sequence of any one of SEQ ID NOS: 2 to 4 and having a sequence identity of at least 80% to the amino acid sequence of any one of SEQ ID NOS: 2 to 4.

In certain embodiments, the method of the present invention further includes producing the electron transfer protein by expressing at least one DNA selected from (G), (H), and (I), wherein (G), (H), and (I) are as follows:

(G) a DNA having a nucleotide sequence of SEQ ID NO: 9, (H) a DNA that has a nucleotide sequence having a sequence identity of at least 90% to a nucleotide sequence of SEQ ID NO: 9, and (I) a DNA hybridizable, under stringent conditions, with a DNA having a nucleotide sequence complementary to a nucleotide sequence of SEQ ID NO: 9.

In another aspect of the present invention, there is provided a recombinant vector for converting α-guaiene to (−)-rotundone, the recombinant vector including:

a DNA recited in any one of the above (g), (h), (i), (j), and (k); or a DNA recited in any one of the above (g), (h), (i), (j), (k), (l), (m), (n), (o), and (p), and a DNA recited in any one of the above (G), (H), and (I), wherein (G), (H), and (I).

In further aspect of the present invention, there is provided a transformant for converting α-guaiene to (−)-rotundone, the transformant including the recombinant vector recited above.

EXAMPLES

Hereinafter, the present invention will be more specifically described with reference to examples. It will be understood that the examples are not intended to limit the present invention.

(1) Preparation of Recombinant *Escherichia coli* Containing Introduced Gene Encoding Cytochrome P450 Protein A gene (cypC (also called ybdT), SEQ ID NO: 5) encoding *Bacillus subtilis*-derived CYP152A1 (SEQ ID NO: 1), a gene (pksS, SEQ ID NO: 6) encoding *Bacillus subtilis*-derived CYP107K1 (SEQ ID NO: 2), a gene (SEQ ID NO: 7) encoding *Bacillus cereus*-derived CYP106 (BCE_2659) (SEQ ID NO: 3), and a gene (cypA, SEQ ID NO: 8) encoding *Bacillus cereus*-derived CYP107 (BCE_2696) (SEQ ID NO: 4) were selected as genes encoding cytochrome P450 proteins.

A plasmid vector was prepared by inserting any one of the selected four genes into vector pET21a or pET21d (all manufactured by Invitrogen), and another plasmid vector was prepared by inserting Pdx and PdR genes, i.e., *Pseudomonas putida*-derived redox partner protein genes (camA and camB, SEQ ID NO: 9) into vector pMW218. These vectors were introduced into an *Escherichia coli* BL21 (DE3) strain.

More specific procedures were as follows.

For cypC and pksS, the gene was inserted into the pET21a plasmid using restriction enzyme NdeI and the restriction enzyme shown below. To insert the CYP107K1 gene (i.e., pksS), the NdeI cleavage site of the vector was blunted with T4 DNA polymerase before ligation.

For the gene encoding CYP106 (BCE_2659) and cypA, the gene was inserted into the pET21a vector using restriction enzyme NdeI and the restriction enzyme shown below.

For Pdx and PdR genes, the pMW218 plasmid (NIPPON GENE CO., LTD.) was cleaved with NdeI and the restriction enzymes shown below (HindIII or SacI), and then the genes were inserted into the plasmid.

The sequence of the primers used to the amplification of each gene and the restriction enzymes used the introduction of each gene are as shown below. The primer sequence is shown from 5'- to 3'-end.

```
CYP152A1 (cypC)
Forward primer:
                                     (SEQ ID NO: 12)
GAATTCCATATGAATGAGCAGATTCCACAT
Restriction enzyme: NdeI Reverse primer:
                                     (SEQ ID NO: 13)
CGCCTGATCCTTAACTTTTTCGTCTGATTCC
Restriction enzyme: BamHI CYP107K1 (pksS)
Forward primer:
                                     (SEQ ID NO: 14)
TGCAAATGGAAAAATTGATGTTTC
(Blunt)

Reverse primer:
                                     (SEQ ID NO: 15)
CGCGGATCCTTATTTTGAAAGTGAAACAGG
Restriction enzyme: BamHI Pdx (camA)
Forward primer:
                                     (SEQ ID NO: 16)
TTCCATATGTCTAAAGTAGTGTATGTGTCA
Restriction enzyme: NdeI Reverse primer:
                                     (SEQ ID NO: 17)
CACAAGCTTTTACCATTGCCTATCGGGAAC
Restriction enzyme: HindIII PdR (camB)
Forward primer:
                                     (SEQ ID NO: 18)
TTCCATATGAACGCAAACGACAACGTGGTC
Restriction enzyme: NdeI Reverse primer:
                                     (SEQ ID NO: 19)
CACGAGCTCTCAGGCACTACTCAGTTCAGC
Restriction enzyme: SacI CYP106 (BCE_2659) ORF
Forward primer:
                                     (SEQ ID NO: 20)
GAATTCCATATGGCTTCGCCTGAAAATGTG
Restriction enzyme: NdeI Reverse primer:
                                     (SEQ ID NO: 21)
CGCGGATCCTTATTGAGTTTTTAAGCAGAT
Restriction enzyme: BamHI
```

-continued

```
CYP107 (BCE_2696) ORF (cypA)
Forward primer:
                                           (SEQ ID NO: 22)
GAATTCCATATGAAAAAACTAACTTTTAAC
Restriction enzyme: NdeI Reverse primer:
                                           (SEQ ID NO: 23)
CCGGAATTCTTAGAAAATAACTGGTAGACT
Restriction enzyme: EcoRI
```

Each resulting recombinant plasmid vector was introduced into an *Escherichia coli* DH5a strain (TAKARA BIO INC.) and amplified. The amplified recombinant plasmid vector was sequenced to confirm that the construct of interest was obtained.

(2) Identification of α-Guaiene Conversion Product

The prepared recombinant *E. coli* cells were inoculated to an LB medium (containing 1% (w/v) trypton, 0.5% (w/v) yeast extract, and 1% (w/v) NaCl, pH 7.0) containing ampicillin and kanamycin each at a concentration of 100 µg/ml and then cultured in the medium at 30° C. for 6 hours until $OD_{600}$ reached 0.8 to 1.0. Subsequently, isopropyl-R-D-thiogalactopyranoside (IPTG), iron sulfate (II), and 5-aminolevulinic acid were added at final concentrations of 1 mM, 0.5 mM, and 0.5 mM, respectively, to the medium. The cells were then further cultured at 25° C. for 15 hours, so that the expression of the cytochrome P450 gene was induced. After the cultivation for 15 hours, the recombinant *E. coli* cells were collected and washed with a potassium phosphate buffer (50 mM, pH 7.5) containing 10% (v/v) glycerol. The washed *E. coli* cells were suspended in a potassium phosphate buffer with the same composition. The suspension was used for the reaction of α-guaiene with the cultured recombinant *E. coli* cells.

Specifically, 250 µl of a reaction liquid was prepared, the reaction liquid containing the recombinant *E. coli* cells (the amount of cells corresponded to that collected from 2 ml of the culture liquid), 5 mM of α-guaiene, 5% (v/v) dimethylsulfoxide (DMSO as a solvent for dissolving the substrate in the reaction liquid), 10% (v/v) glycerol, and 50 mM of a potassium phosphate buffer (pH 7.5). The reaction liquid was shaken at 30° C. for 17 hours.

After the shaking for 17 hours, 2.5 µl of 5 N HCl and 1 ml of ethyl acetate were added to the reaction liquid, and then extraction was performed on the reaction liquid. The resulting liquid extract was subjected to GC-MS analysis. The GC-MS analysis was performed using Agilent 6890 Series GC system and 5973 Network Mass Selective Detector (all manufactured by Agilent Technologies, Inc.) and InertCap 5MS/GL Column (manufactured by GL Sciences Inc.) under the following conditions: sample injection volume, 1 µl; split ratio, 4:1; carrier gas, He (1.2 ml/min); injection port temperature, 270° C.; initial oven temperature, 80° C.; initial time, 2 minutes; rate of temperature increase, 10° C./min; final temperature, 300° C.

Figure 2:
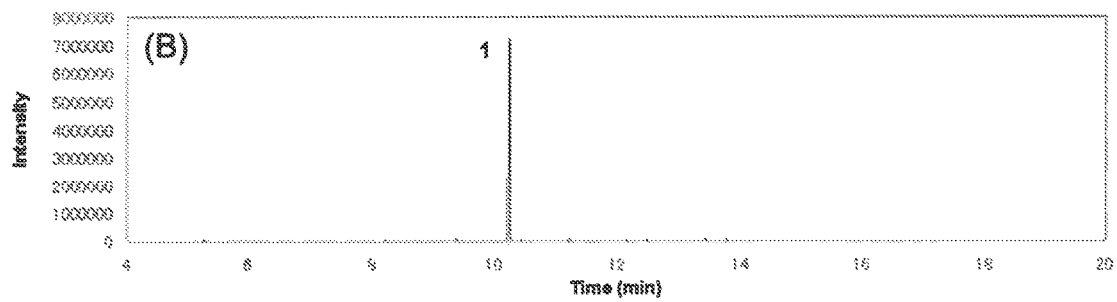
FIG. 2 shows the result of GC-MS analysis of the extraction of the reaction liquid in which α-guaiene was reacted with the *E. coli* cells not carrying CYP152A1.

As a result, an α-guaiene peak and a new peak expected to correspond to an α-guaiene conversion product were detected for all of the four recombinant *E. coli* strains. FIG. 1 shows the results on CYP152A1 as a typical example. It was demonstrated that CYP152A1, which is known to require no redox partner protein, exhibited the oxidation activity even in the presence of putidaredoxin and putidaredoxin reductase. In FIG. 1, peak 1 corresponds to the α-guaiene peak, and peak 2 corresponds to the new peak (at a retention time of 13.4 minutes). The retention time of the new peak agreed with the retention time of a rotundone standard. On the other hand, recombinant *E. coli* cells carrying introduced empty vectors, i.e., pET21a and pMW218 plasmids with no inserted gene, were prepared as a control and then cultured under the conditions shown above. The cultured cells were allowed to react with α-guaiene and then subjected to the extraction and analysis as described above, but the new peak was not detected (FIG. 2).

Figure 3:
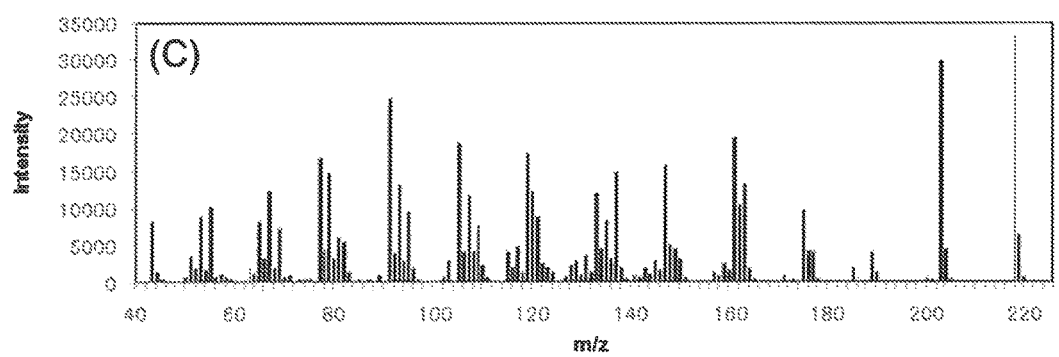
FIG. 3 shows the result of MS spectrum analysis of the α-guaiene conversion product.

The MS spectrum of the α-guaiene conversion product was measured. The resulting parent ion peak had an m/z value of 218.2, which agreed with the molecular weight of rotundone (FIG. 3).

These experiments demonstrate that the selected four genes enable the selective conversion of α-guaiene to rotundone with high efficiency and high purity.

(3) Quantification of Rotundone Produced by Conversion of α-Guaiene

A calibration curve was drawn using a rotundone standard. The concentration of the α-guaiene conversion product, rotundone, was calculated based on the calibration curve.

The quantification showed that the cultured recombinant *E. coli* cells carrying the introduced genes, i.e., the recombinant cells carrying the CYP152A1-encoding gene, the recombinant cells carrying the CYP107K1-encoding gene, the recombinant cells carrying the CYP106 (BCE_2659)-encoding gene, and the recombinant cells carrying the CYP107 (BCE_2696)-encoding gene, produced 0.41 mM, 0.33 mM, 0.36 mM, and 0.36 mM of rotundone, respectively, from the reaction liquid containing 5 mM of α-guaiene after the reaction for 17 hours.

What is claimed is:

1. A method of producing (−)-rotundone from α-guaiene, the method comprising the following steps (1) and/or (2):
   (1) allowing a cytochrome P450 protein to act on α-guaiene, which cytochrome P450 (CYP) protein belongs to a CYP152 family and converts α-guaiene to rotundone,
   wherein the cytochrome P450 protein is SEQ ID NO:1, or a protein sequence having a sequence identity of at least 90% to the amino acid sequence of SEQ ID NO:1;
   (2) allowing a cytochrome P450 protein to act on α-guaiene in the presence of an electron transfer protein capable of transferring electrons to the cytochrome P450 protein, which cytochrome P450 (CYP) protein belongs to a CYP152, CYP106, or CYP107 family and converts α-guaiene to rotundone,
   wherein the cytochrome P450 protein is selected from the protein sequences of SEQ ID NOs:1 to 4, or a protein sequence having a sequence identity of at least 90% to an amino acid sequence of any of SEQ ID NOs:1 to 4.

2. The method according to claim 1, wherein the cytochrome P450 protein in the step (1) is *Bacillus subtilis*-derived CYP152A1 (SEQ ID NO:1), and the cytochrome P450 protein in the step (2) is at least one selected from the group consisting of *Bacillus subtilis*-derived CYP152A1 (SEQ ID NO:1) and CYP107K1 (SEQ ID NO:2), and *Bacillus cereus*-derived CYP106 (BCE_2659) (SEQ ID NO:3) and CYP107 (BCE_2696) (SEQ ID NO:4).

3. The method according to claim 1, wherein the electron transfer protein is a combination of ferredoxin and ferredoxin reductase.

4. The method according to claim 1, wherein the electron transfer protein is a combination of at least one selected from (A) and (B) and at least one selected from (C) and (D), wherein (A), (B), (C) and (D) are as follows:

(A) a protein having an amino acid sequence of SEQ ID NO: 10;

(B) a protein that has an amino acid sequence having a sequence identity of at least go % to an amino acid sequence of SEQ ID NO: 10;

(C) a protein having an amino acid sequence of SEQ ID NO: 11;

(D) a protein that has an amino acid sequence having a sequence identity of at least 90% to an amino acid sequence of SEQ ID NO: 11.

5. The method according to claim 1, further comprising: producing the cytochrome P450 protein for the step (1) by expressing at least one DNA selected from (g), (h), (i) and (j); and/or producing the cytochrome P450 protein for the step (2) by expressing at least one DNA selected from (g), (h), (i) and (j) wherein (g), (h), (i) and (j) are as follows:

(g) a DNA having a nucleotide sequence of SEQ ID NO: 5;

(h) a DNA that has a nucleotide sequence having a sequence identity of at least 90% to a nucleotide sequence of SEQ ID NO: 5

(i) a DNA having a nucleotide sequence of any one of SEQ ID NOS: 6 to 8;

(j) a DNA that has a nucleotide sequence having a sequence identity of at least 90% to a nucleotide sequence of any one of SEQ ID NOS: 6 to 8.

6. The method according to claim 1, further comprising: producing the electron transfer protein by expressing at least one DNA selected from (G) and (H), wherein (G) and (H) are as follows:

(G) a DNA having a nucleotide sequence of SEQ ID NO: 9, (H) a DNA that has a nucleotide sequence having a sequence identity of at least 90% to a nucleotide sequence of SEQ ID NO: 9.

7. The method of claim 5, wherein the DNA of SEQ ID NOs:5-8 are transformed in *E. coli* cells.

8. The method of claim 6, wherein the DNA of SEQ ID NO:9 is transformed in *E. coli* cells.

* * * * *